(12) United States Patent
Rabinow et al.

(10) Patent No.: US 10,952,965 B2
(45) Date of Patent: Mar. 23, 2021

(54) COMPOSITIONS AND METHODS FOR DRUG DELIVERY

(75) Inventors: Barrett Rabinow, Skokie, IL (US); Shawn F. Bairstow, Gurnee, IL (US); Mahesh V. Chaubal, Lake Zurich, IL (US); Sarah Lee, Buffalo Grove, IL (US); Jane Werling, Arlington Heights, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 603 days.

(21) Appl. No.: 12/467,230

(22) Filed: May 15, 2009

(65) Prior Publication Data
US 2010/0290983 A1 Nov. 18, 2010

(51) Int. Cl.
| | |
|---|---|
| A61K 9/14 | (2006.01) |
| A61K 31/337 | (2006.01) |
| A61K 31/496 | (2006.01) |
| A61K 31/513 | (2006.01) |
| A61K 31/415 | (2006.01) |
| A61K 31/551 | (2006.01) |
| A61K 31/538 | (2006.01) |
| A61K 31/365 | (2006.01) |
| A61K 31/4725 | (2006.01) |
| A61K 47/34 | (2017.01) |
| A61K 31/444 | (2006.01) |
| A61K 31/7068 | (2006.01) |
| A61K 31/7072 | (2006.01) |
| A61K 31/427 | (2006.01) |
| A61K 31/708 | (2006.01) |

(52) U.S. Cl.
CPC ............ *A61K 9/145* (2013.01); *A61K 31/337* (2013.01); *A61K 31/365* (2013.01); *A61K 31/415* (2013.01); *A61K 31/427* (2013.01); *A61K 31/444* (2013.01); *A61K 31/4725* (2013.01); *A61K 31/496* (2013.01); *A61K 31/513* (2013.01); *A61K 31/538* (2013.01); *A61K 31/551* (2013.01); *A61K 31/708* (2013.01); *A61K 31/7068* (2013.01); *A61K 31/7072* (2013.01); *A61K 47/34* (2013.01); *Y02A 50/30* (2018.01)

(58) Field of Classification Search
CPC ...... A61K 9/145; A61K 47/34; A61K 31/365; A61K 31/415; A61K 31/427; A61K 31/444; A61K 31/337; A61K 31/7072; A61K 31/7068; A61K 31/513; A61K 31/708; A61K 31/496; A61K 31/551; A61K 31/4725; A61K 31/538; A61P 3/10; A61P 5/14; A61P 31/06; A61P 35/00; A61P 35/02; A61P 21/04; A61P 25/28; A61P 31/10; A61P 31/18; A61P 31/14; A61P 31/00; A61P 31/20; A61P 31/04; A61P 29/00; A61P 33/06; A61P 15/08; A61P 25/16; A61P 25/00; A61P 19/02; A61P 25/14; A61P 31/16; A61P 37/02; A61P 33/02; Y02A 50/30; Y02A 50/471; Y02A 50/411; Y02A 50/385
USPC ................................. 424/489, 490, 491, 498
See application file for complete search history.

(56) References Cited

U.S. PATENT DOCUMENTS

| | | |
|---|---|---|
| 4,224,313 A | 9/1980 | Zimmermann et al. |
| 4,269,826 A | 5/1981 | Zimmermann et al. |
| 4,289,756 A | 9/1981 | Zimmermann et al. |
| 4,608,278 A | 8/1986 | Frank et al. |
| 4,670,185 A | 6/1987 | Fujiwara et al. |
| 4,826,689 A | 5/1989 | Violanto |
| 4,973,465 A | 11/1990 | Baurain et al. |
| 4,997,454 A | 3/1991 | Violante et al. |
| 5,091,188 A | 2/1992 | Haynes |
| 5,100,591 A | 3/1992 | Leclef et al. |
| 5,118,528 A | 6/1992 | Fessi et al. |
| 5,145,684 A | 9/1992 | Liversidge et al. |
| 5,188,837 A | 2/1993 | Domb |
| 5,212,162 A | 5/1993 | Missel et al. |
| 5,560,932 A | 10/1996 | Bagchi et al. |
| 5,662,883 A | 9/1997 | Bagchi et al. |
| 5,665,331 A | 9/1997 | Bagchi et al. |

(Continued)

FOREIGN PATENT DOCUMENTS

| | | |
|---|---|---|
| EP | 1952825 A1 | 8/2008 |
| GB | 1438973 A | 6/1976 |

(Continued)

OTHER PUBLICATIONS

Kalra et al., Pharm. Res., 2006, 23(12), p. 2809-2817.*

(Continued)

*Primary Examiner* — Michael G. Hartley
*Assistant Examiner* — Leah H Schlientz
(74) *Attorney, Agent, or Firm* — K&L Gates LLP

(57) ABSTRACT

The present disclosure is directed to surface-modified particles and to methods of making and using the same. The surface-modified particles comprise a particle core and a coating associated with the particle core, wherein the particle core comprises an active agent, the coating comprises a surfactant having formula I, and the surface-modified particle has an average size from about 1 nm to about 2,000 nm:

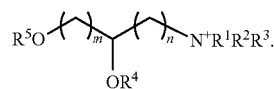

41 Claims, 6 Drawing Sheets

(56) References Cited

U.S. PATENT DOCUMENTS

| | | | |
|---|---|---|---|
| 5,716,642 | A | 2/1998 | Bagchi et al. |
| 5,720,551 | A | 2/1998 | Shechter |
| 5,780,062 | A | 7/1998 | Frank et al. |
| 5,792,451 | A | 8/1998 | Sarubbi et al. |
| 5,981,719 | A | 11/1999 | Woiszwillo et al. |
| 6,090,925 | A | 7/2000 | Woiszwillo et al. |
| 6,143,211 | A | 11/2000 | Mathiowitz et al. |
| 6,235,224 | B1 | 5/2001 | Mathiowitz et al. |
| 6,268,053 | B1 | 7/2001 | Woiszwillo et al. |
| 6,331,299 | B1 | 12/2001 | Rothman et al. |
| 6,455,073 | B1 | 9/2002 | Meredith et al. |
| 6,458,387 | B1 | 10/2002 | Scott et al. |
| 6,607,784 | B2 | 8/2003 | Kipp et al. |
| 6,616,869 | B2 | 9/2003 | Mathiowitz et al. |
| 6,632,671 | B2 | 10/2003 | Unger |
| 6,638,621 | B2 | 10/2003 | Anderson |
| 6,645,464 | B1 | 11/2003 | Hainfeld |
| 6,676,972 | B2 | 1/2004 | Meredith et al. |
| 6,790,455 | B2 | 9/2004 | Chu et al. |
| 6,835,396 | B2 | 12/2004 | Brynjelsen et al. |
| 6,869,617 | B2 | 3/2005 | Kipp et al. |
| 6,884,436 | B2 | 4/2005 | Kipp et al. |
| 6,902,743 | B1 | 6/2005 | Setterstrom et al. |
| 7,037,528 | B2 | 5/2006 | Kipp et al. |
| 7,217,735 | B1* | 5/2007 | Au ............... A61K 9/1272 514/456 |
| 7,338,657 | B2 | 3/2008 | Vogel et al. |
| 7,374,782 | B2 | 5/2008 | Brown |
| 2002/0034537 | A1* | 3/2002 | Schulze et al. ............ 424/450 |
| 2002/0136769 | A1* | 9/2002 | Kabanov ............ A61K 9/5138 424/487 |
| 2002/0164694 | A1 | 11/2002 | Moore et al. |
| 2003/0092069 | A1 | 5/2003 | Kuroda et al. |
| 2003/0099675 | A1* | 5/2003 | Jeong ................. A61K 9/1075 424/400 |
| 2004/0022861 | A1 | 2/2004 | Williams et al. |
| 2004/0062756 | A1 | 4/2004 | Laurent et al. |
| 2004/0175429 | A1* | 9/2004 | Alavattam ........ A61K 9/1617 424/490 |
| 2005/0037083 | A1 | 2/2005 | Brynjelsen et al. |
| 2005/0048002 | A1 | 3/2005 | Rabinow et al. |
| 2005/0084456 | A1 | 4/2005 | Tang et al. |
| 2005/0112141 | A1 | 5/2005 | Terman |
| 2005/0244503 | A1* | 11/2005 | Rabinow et al. ............ 424/489 |
| 2006/0073199 | A1 | 4/2006 | Chaubal et al. |
| 2007/0172653 | A1* | 7/2007 | Berkland ............ A61K 9/0019 428/402 |
| 2009/0047337 | A1 | 2/2009 | Mescheder et al. |
| 2010/0172943 | A1* | 7/2010 | Edelson et al. ............ 424/401 |
| 2010/0226970 | A1 | 9/2010 | McDonald et al. |
| 2010/0255103 | A1* | 10/2010 | Liong ................ A61K 9/5094 424/489 |
| 2011/0244002 | A1* | 10/2011 | Shen ................. A61K 9/143 424/400 |
| 2011/0268791 | A1* | 11/2011 | Liu ................... A61K 49/005 424/450 |

FOREIGN PATENT DOCUMENTS

| | | |
|---|---|---|
| JP | 60-150826 | 8/1985 |
| JP | 2003/514768 A | 4/2003 |
| JP | 2008/540364 A | 11/2008 |
| RU | 2003108736 | 7/2006 |
| WO | WO-92/11846 | 7/1992 |
| WO | WO-92/017214 | 10/1992 |
| WO | WO-94/007999 | 4/1994 |
| WO | WO-97/14407 | 4/1997 |
| WO | WO-98/001162 | 1/1998 |
| WO | WO-98/47492 | 10/1998 |
| WO | WO-99/13054 | 3/1999 |
| WO | WO-00/64954 | 11/2000 |
| WO | WO-01/58431 | 8/2001 |
| WO | WO-01/82899 A2 | 11/2001 |
| WO | WO-02/055059 | 7/2002 |
| WO | WO-02/060416 | 8/2002 |
| WO | WO-02/082074 | 10/2002 |
| WO | WO-2004/017907 A2 | 3/2004 |
| WO | WO-2004/035768 | 4/2004 |
| WO | WO-04/112747 | 12/2004 |
| WO | WO-2004/110270 | 12/2004 |
| WO | WO-2004/112747 | 12/2004 |
| WO | WO-2005/016246 | 2/2005 |
| WO | WO-2005/059118 | 6/2005 |
| WO | WO-2005/072706 | 8/2005 |
| WO | WO-2005/079854 | 9/2005 |
| WO | WO-2005/123907 | 12/2005 |
| WO | WO-2006/080243 A1 | 8/2006 |
| WO | WO-2007/048326 A1 | 5/2007 |
| WO | WO-2007/055995 | 5/2007 |

OTHER PUBLICATIONS

Liu et al., JACS, 2009, 131, p. 1354-1355.*
Bergna et al., Collidal Silica, Chapter 27 (pp. 311-329), 2005, Taylor and Francis.*
Solid, http://www.merriam-webster.com/dictionary/solid, accessed Feb. 25, 2016.*
Huang et al., Nanomater. Nanotechnol., 2014, 4(2), p. 1-15.*
Wang, Microporous and Mesoporous Materials, 2009, 117, p. 1-9.*
Stubbe, "Evaluation of Degrading Dextran Hydrogels To Obtain Pulsed Drug Delivery," 2004, PhD thesis, Universiteit Gent. (Year: 2004).*
Van Thienen et al., Macromolecules, 2005, 38, p. 8503-8511. (Year: 2005).*
Mornet et al., Nano Letters, 2005, 5, p. 281-285. (Year: 2005).*
Singh, ACS Nano, 2008, 2(5), p. 1040-50. (Year: 2008).*
Van Thienen, International Journal of Pharmaceutics, 2008, 351, p. 174-185. (Year: 2008).*
Wang et al., J Drug Target., 2005, 13(1), p. 73-80. (Year: 2005).*
Ginsburg et al. "Role of leukocyte factors and cationic polyelectrolytes in phagocytosis of group A Streptococci and *Candida albicans* by neutrophils, macrophages, fibroblasts and epithelial cells: Modulation by anionic polyelectrolytes in relation to pathogenesis of chronic inflammation", *Inflammation*, 5: 289-312 (1981).
Dou et al., Macrophage delivery of nanoformulated antiretroviral drug to the brain in a murine model of neuroAIDS, *J. Immunol.*, 183:611-9 (2009).
Nowacek et al., NanoART synthesis, characterization, uptake, release and toxicology for human monocyte-macrophage drug delivery, *Nanomedicine*, 4:903-17 (2009).
Coester et al., Preparation of avidin-labelled gelatin nanoparticles as carriers for biotinylated peptide nucleic acid (PNA), *Int. J. Pharm.*, 196:147-9 (2000).
D'Souza et al., Site specific microencapsulated drug targeting strategies—liver and gastro-intestinal tract targeting, *Adv. Drug Delivery Rev.*, 17:247-54 (1995).
Kreuter, Nanoparticulate systems for brain delivery of drugs, *Adv. Drug Deliv. Rev.*, 47:65-81 (2001).
Mishra et al., Engineered human erythrocytes as carriers for ciprofloxacin, *Drug Delivery*, 3:239-44 (1996).
Mishra et al., Surface modified methotrexate loaded erythrocytes for enhanced macrophage uptake, *J. Drug Target*, 8:217-24 (2000).
Issekutz et al., The in vivo quantitation and kinetics of monocyte migration into acute inflammatory tissue, *Am. J. Pathol.*, 103:47-55 (1981).
"Dipolar aprotic solvent", *IUPAC Compendium of Chemical Terminology*, International Union of Pure and Applied Chemistry, 2nd ed. (1997).
Allen et al., "Critical evaluation of acute cardiopulmonary toxicity of microspheres", *J. Nucl. Med.*, 19:1204-8 (1987).
Aquaro et al., "Macrophages and HIV infection: therapeutical approaches toward this strategic virus reservoir", *Antiviral Res.*, 55:209-25 (2002).
Audran et al., "Fate of mouse macrophages radiolabelled with PKH-95 and injected intravenously", *Nucl. Med. Biol.*, 22:817-21 (1995).

(56) References Cited

OTHER PUBLICATIONS

Beduneau et al., "Active targeting of brain tumors using nanocarriers", *Biomaterials*, 28:4947-67 (2007).
Beduneau et al., "Brain targeting using novel lipid nanovectors", *J. Control. Release*, 126:44-9 (2008).
Beduneau et al., "Design of targeted lipid nanocapsules by conjugation of whole antibodies and antibody Fab' fragments", *Biomaterials*, 28:4978-90 (2007).
Beduneau et al., "Facilitated monocyte-macrophage uptake and tissue distribution of superparamagnetic iron-oxide nanoparticles," *PLoS ONE*, 4:e4343 (12 pp.) (2009).
Beduneau et al., "Human monocyte uptake and carriage of IgG-coated nanoparticles to neuroinflamed brain subregions," Abstract from NSTI Nanotech 2008 Conference Program (Boston, Mass.) (Jun. 1-5, 2008).
Bender et al., "Efficiency of nanoparticles as a carrier for antiviral agents in human immunodeficiency virus-infected human monocytes/macrophages in vitro", *Antimicrob. Agents Chemother.*, 40:1467-71 (1996).
Betageri et al., "Fc-receptor-mediated targeting of antibody-bearing liposomes containing dideoxycytidine triphosphate to human monocyte/macrophages", *J. Pharm. Pharamcol.*, 45:48-53 (1993).
Bromberg et al., "Insulin particle formation in supersaturated aqueous solutions of poly(ethylene glycol)", *Biophys. J.*, 89:3424-33 (2005).
Campbell, "Tumor physiology and delivery of nanopharmaceuticals", *Anticancer Agents Med. Chem.*, 6:503-12 (2006).
Carver et al., "Caveolae: mining little caves for new cancer targets", *Nat. Rev. Cancer*, 3:571-81 (2003).
Choi et al., "A cellular Trojan Horse for delivery of therapeutic nanoparticles into tumors", *Nano Lett.*, 7:3759-65 (2007).
Choi et al., "Hydrophobic ion pair formation between leuprolide and sodium oleate for sustained release from biodegradable polymeric microspheres", *Int. J. Pharm.*, 203:193-202 (2000).
Cibrowski et al., "Human immunodeficiency virus-mononuclear phagocyte interactions: emerging avenues of biomarker discovery, modes of viral persistence and disease pathogenesis", *Curr. HIV Res.*, 4:279-91 (2006).
Connor et al., "Fc receptors for IgG (Fc gamma Rs) on human monocytes and macrophages are not infectivity receptors for human immunodeficiency virus type 1 (HIV-1): studies using bispecific antibodies to target HIV-1 to various myeloid cell surface molecules, including the Fc gamma R", *Proc. Natl. Acad. Sci. USA*, 88:9593-7 (1991).
Constancis et al., "Macromolecular colloids of diblock poly(amino acids) that bind insulin", *J. Colloid Interface Sci.*, 217:357-68 (1999).
Crowe et al., "The contribution of monocyte infection and trafficking to viral persistence, and maintenance of the viral reservoir in HIV infection", *J. Leukoc. Biol.*, 74:635-41 (2003).
Dai et al., "Characterization of physiochemical and biological properties of an insulin/lauryl sulfate complex formed by hydrophobic ion pairing", *Int. J. Pharm.*, 336:58-66 (2007).
Daleke et al., "Endocytosis of liposomes by macrophages: binding, acidification and leakage of liposomes monitored by a new fluorescence assay", *Biochim. Biophys. Acta.*, 1024:352-66 (1990).
Davis et al., "Pulmonary perfusion imaging: acute toxicity and safety factors as a function of particle size", *J. Nucl. Med.*, 19:1209-13 (1978).
Dilworth et al., "Molecular targets for emerging anti-tumor therapies for neurofibromatosis type 1", *Biochem. Pharmacol.*, 72:1485-92 (2006).
Dobrovolskaia et al., "Preclinical studies to understand nanoparticle interaction with the immune system and its potential effects on nanoparticle biodistribution", *Mol. Pharm.*, 5:487-95 (2008).
Dou et al., "Development of a macrophage-based nanoparticle platform for antiretroviral drug delivery", *Blood*, 108:2827-35 (2006).

Dou et al., "Laboratory investigations for the morphologic, pharmacokinetic, and anti-retroviral properties of indinavir nanoparticles in human monocyte-derived macrophages", *Virology*, 358:148-58 (2007).
Dutta et al., "Poly (propyleneimine) dendrimer based nanocontainers for targeting of efavirenz to human monocytes/macrophages in vitro", *J. Drug Target*, 15:89-98 (2007).
Engberink et al., "MRI of monocyte infiltration in an animal model of neuroinflammation using SPIO-labeled monocytes or free USPIO", *J. Cereb. Blood Flow Metab.*, 28:841-51 (2008).
Fischer-Smith et al., "CNS invasion by CD14+/CD16+ peripheral blood-derived monocytes in HIV dementia: perivascular accumulation and reservoir of HIV infection", *J. Neurovirol.*, 7:528-41 (2001).
Fujiwara et al., "[From the immunological aspect—interleukin-10 production by human blood mononuclear cells stimulated with multidrug-resistant *Mycobacterium* tuberculosis]", *Kekkaku*, 71:43-6 (1996).
Gorantla et al., "Quantitative magnetic resonance and SPECT imaging for macrophage tissue migration and nanoformulated drug delivery", *J. Leukoc. Biol.*, 80:1165-74 (2006).
*Handbook of Pharmaceutical Excipients*, American Pharmaceutical Association and The Pharmaceutical Society of Great Britain, London, England: The Pharmaceutical Press 1986.
Hanemann, "Magic but treatable? Tumours due to loss of merlin", *Brain*, 131:606-15 (2007).
Heiati et al., "Solid lipid nanoparticles as drug carriers: II. Plasma stability and biodistribution of solid lipid nanoparticles containing the lipophilic prodrug 3'-azido-3'-deoxythymidine palmitate in mice", *Int. J. Pharmaceutics*, 174:71-80 (1998).
Holevinsky et al., "Membrane capacitance changes associated with particle uptake during phagocytosis in macrophages", *Biophys. J.*, 75:2577-86 (1998).
Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): implications for HIV-1 infections of humans", *Proc. Natl. Acad. Sci. USA*, 98:658-663 (2001).
Jain et al., "RGD-anchored magnetic liposomes for monocytes/neutrophils-mediated brain targeting", *Int. J. Pharm.*, 261:43-55 (2003).
Kadiu et al., "Mononuclear phagocytes in the pathogenesis of neurodegenerative diseases", *Neurotox. Res.*, 8:25-50 (2005).
Kennedy et al., "Mature monocytic cells enter tissues and engraft", *Proc. Natl. Acad. Sci. USA*, 95:14944-9 (1998).
Khan et al., "Enhanced anticryptococcal activity of chloroquine in phosphatidylserine-containing liposomes in a murine model", *J. Antimicrob. Chemother.*, 55:223-8 (2005).
Kingsley et al., "Nanotechnology: a focus on nanoparticles as a drug delivery system", *J. Neuroimmune Pharmacol.*, 1:340-50 (2006).
Kinman et al., "Lipid-drug association enhanced HIV-1 protease inhibitor indinavir localization in lymphoid tissues and viral load reduction: a proof of concept study in HIV-2287-infected macaques", *J. Acquir. Immune Defic. Syndr.*, 34:387-97 (2003).
Korf, "Determination of end points for treatment of neurofibromatosis 1", *J. Child Neurol.*, 17:642-5 (2002).
Kuwata et al., "Contribution of monocytes to viral replication in macaques during acute infection with simian immunodeficiency virus", *AIDS Res. Hum. Retroviruses*, 23:372-80 (2007).
Lee et al., "Novel molecular approaches to cystic fibrosis gene therapy", *Biochem. J.*, 387:1-15 (2005).
Limoges et al., "Sustained antiretroviral activity of indinavir nanosuspensions in primary monocyte-derived macrophages" poster presentation, 11th Conference on Retroviruses and Opportunistic Infections, Feb. 8-11, 2004.
Liu et al., "Ingress of blood-borne macrophages across the blood-brain barrier in murine HIV-1 encephalitis", *J. Neuroimmunol.*, 200:41-52 (2008).
Lobenberg et al., "Body distribution of azidothymidine bound to hexyl-cyanoacrylate nanoparticles after i.v. injection to rats", *J. Control Release*, 50:21-30 (1998).

(56) References Cited

OTHER PUBLICATIONS

Lobenberg et al., "Macrophage targeting of azidothymidine: a promising strategy for AIDS therapy", *AIDS Res. Hum. Retroviruses*, 12:1709-15 (1996).
Maccollin et al., "Establishing priorities in neurofibromatosis research: a workshop summary", *Genetics in Medicine*, 3:212-217 (2001).
Malcolmson et al., "Dry powder formulations for pulmonary delivery", *Pharm. Sci. Tech. Today*, 1: 394-8 (1998).
Manjunath et al., "Pharmacokinetics, tissue distribution and bioavailability of nitrendipine solid lipid nanoparticles after intravenous and intraduodenal administration", *J. Drug Target*, 14:632-45 (2006).
Margel et al., "Polyacrolein microspheres as a new tool in cell biology", *J. Cell. Sci.*, 56:157-75 (1982).
Mehta et al., "Uptake of liposomes and liposome-encapsulated muramyl dipeptide by human peripheral blood monocytes", *J. Reticuloendothel. Soc.*, 32:155-64 (1982).
Marriott, "Pulmonary delivery of peptides and proteins", *Eur. J. Pharm. Sci.*, 4:S34 (1996).
Moffat et al., "Management strategies in neurofibromatosis type 2", *Eur. Arch. Otorhinolaryngol.*, 260: 12-8 (2003).
Moghimi et al., "Capture of stealth nanoparticles by the body's defences", *Crit. Rev. Ther. Drug Carrier Syst.*, 18:527-50 (2001).
Moghimi et al., "Long-circulating and target-specific nanoparticles: theory to practice", *Pharmacol. Rev.*, 53:283-318 (2001).
Moghimi et al., "Recognition by macrophages and liver cells of opsonized phospholipid vesicles and phospholipid headgroups", *Pharm. Res.*, 18:1-8 (2001).
Moghimi et al., "Stealth liposomes and long circulating nanoparticles: critical issues in pharmacokinetics, opsonization and protein-binding properties", *Prog. Lipid Res.*, 42:463-78 (2003).
Nelson et al., "Coregistration of quantitative proton magnetic resonance spectroscopic imaging with neuropathological and neurophysiological analyses defines the extent of neuronal impairments in murine human immunodeficiency virus type-1 encephalitis", *J. Neurosci. Res.*, 80:562-75 (2005).
Nesbit et al., "In vitro and animal models of human immunodeficiency virus infection of the central nervous system", *Clin. Diagn. Lab. Immunol.*, 9:515-524 (2002).
Nishikawa et al., "Scavenger receptor-mediated uptake and metabolism of lipid vesicles containing acidic phospholipids by mouse peritoneal macrophages", *J. Biol. Chem.*, 265:5226-31 (1990).
Nottet et al., "HIV-1 entry into brain: Mechanisms for the infiltration of HIV-1-infected macrophages across the blood-brain barrier", p. 55, in Gendelman (ed.) et al., *The Neurology of AIDS*, New York: Hodder Arnold Publication (1997).
Oude Engberink et al., "Physicochemical characteristics of pentamidine-loaded polymethacrylate nanoparticles: implication in the intracellular drug release in Leishmania major infected mice", *Radiology*, 243:467-74 (2007).
Owen et al., "Mathematical modelling of the use of macrophages as vehicles for drug delivery to hypoxic tumour sites", *J. Theor. Biol.*, 226:377-91 (2004).
Owens et al., "Opsonization, biodistribution, and pharmacokinetics of polymeric nanoparticles", *Int. J. Pharm.*, 307:93-102 (2006).
Ozawa et al., "A novel means of drug delivery: myoblast-mediated gene therapy and regulatable retroviral vectors", *Annu. Rev. Pharmacol Toxicol.*, 40:295-317 (2000).
Packer et al., "Plexiform neurofibromas in NF1: toward biologic-based therapy", *Neurology*, 58:1461-70 (2002).
Panyam et al., "Rapid endo-lysosomal escape of poly(DL-lactide-co-glycolide) nanoparticles: implications for drug and gene delivery", *FASEB J.*, 16:1217-26 (2002).
Paul et al., "Physicochemical characteristics of pentamidine-loaded polymethacrylate nanoparticles: implication in the intracellular drug release in Leishmania major infected mice", *J. Drug Target*, 5:481-90 (1998).
Pereboeva et al., "Cellular vehicles for cancer gene therapy: current status and future potential", *BioDrugs*, 18:361-85 (2004).
Perno et al., "Relative potency of protease inhibitors in monocytes/macrophages acutely and chronically infected with human immunodeficiency virus", *J. Infect. Dis.*, 178:413-422 (1998).
Perry et al., "Inflammation in the nervous system", *Curr. Opin. Neurobiol.*, 5:636-41 (1995).
Pietruska et al., "Evaluation of mCD14 expression on monocytes and the blood level of sCD14 in patients with generalized aggressive periodontitis", *Adv. Med. Sci.*, 51:166-9 (2006).
Ren et al., "Structural basis of DOTMA for its high intravenous transfection activity in mouse", *Gene Therapy*, 7:764-8 (2000).
Riccardi, "The genetic predisposition to and histogenesis of neurofibromas and neurofibrosarcoma in neurofibromatosis Type 1", *Neurosurg. Focus*, 22:E3 (2007) (11 pp.).
Riemer et al., "Colorimetric ferrozine-based assay for the quantitation of iron in cultured cells", *Anal. Biochem.*, 331:370-5 (2004).
Rodriguez et al. "Lysosomes behave as Ca2+-regulated exocytic vesicles in fibroblasts and epithelial cells", *J. Cell Biol.*, 137:93-104 (1997).
Romberg et al., "Effect of liposome characteristics and dose on the pharmacokinetics of liposomes coated with poly(amino acid)s", *Pharm. Res.*, 24:2394-401 (2007).
Sawchuk et al., "Investigation of distribution, transport and uptake of anti-HIV drugs to the central nervous system", *Adv. Drug Deliv. Rev.*, 39:5-31 (1999).
Schroeder et al., "Physiological effects of subvisible microspheres administered intravenously to beagle dogs", *J. Pharm. Sci.*, 67:508-13 (1978).
Solas et al., "Discrepancies between protease inhibitor concentrations and viral load in reservoirs and sanctuary sites in human immunodeficiency virus-infected patients," *Antimicrob. Agents Chemother.*, 47:238-43 (2003).
Spitzenberger et al., "Novel delivery system enhances efficacy of antiretroviral therapy in animal model for HIV-1 encephalitis," *J. Cereb. Blood Flow Metab.*, 27:1033-42 (2007).
Thiele et al., "Evaluation of particle uptake in human blood monocyte-derived cells in vitro. Does phagocytosis activity of dendritic cells measure up with macrophages?", *J. Control. Release*, 76:59-71 (2001).
Von Briesen et al., "Controlled release of antiretroviral drugs", *AIDS Rev.*, 2:31-8 (2000).
Watts et al., "Endocytosis: what goes in and how?", *J. Cell. Sci.*, 103:1-8 (1992).
Yokel et al., "Acute toxicity of latex microspheres", *Toxicol. Lett.*, 9:165-70 (1981).
Zarnitsyn et al., "Physical parameters influencing optimization of ultrasound-mediated DNA transfection", *Ultrasound in Med. & Biol.*, 30:527-38 (2004).
Zelivyanskaya et al., "Tracking superparamagnetic iron oxide labeled monocytes in brain by high-field magnetic resonance imaging", *J. Neurosci. Res.*, 73:284-95 (2003).
Zhu et al., "Evidence for human immunodeficiency virus type 1 replication in vivo in CD14(+) monocytes and its potential role as a source of virus in patients on highly active antiretroviral therapy", *J. Virol.*, 76:707-16 (2002).
International Search Report and Written Opinion for corresponding International Application No. PCT/US2010/034711, dated Sep. 6, 2010.
Munerati et al., Macrophages loaded with doxorubicin by ATP-mediated permeabilization: potential carriers for antitumor therapy, *Biochimica et Biophysicia Acta*, 1224:269-76 (1994).
Soma et al., Investigation of the role of macrophages on the cytotoxicity of doxorubicin and doxorubicin-loaded nanoparticles on M5076 cells in vitro, *J. Controlled Release*, 68:281-9 (2000).
Thiele et al., Competitive adsorption of serum proteins at microparticles affects phagocytosis by dendritic cells, Biomaterials, 24:1409-18 (2003).
Notice of Preliminary Rejection (English translation), Korean Patent Application No. 10-2011-7029923, dated Jul. 1, 2016.
Zhu et al., Preparation of novel hollow mesoporous silica spheres and their sustained-release property. *Nanotechnology* 16: 2633-2638 (2005).
Examination Report, Indian patent application No. 9438/DELNP/2011, dated Aug. 16, 2017.

(56) References Cited

OTHER PUBLICATIONS

Brazil Office Action dated Apr. 14, 2020 for App. No. PI1010903-0 (11 pages).

* cited by examiner

1 Day of Culture

1 Day of Culture

2 Days of Culture

2 Days of Culture

6 Days of Culture

6 Days of Culture

COMPOSITIONS AND METHODS FOR DRUG DELIVERY

BACKGROUND

Field of the Disclosure

The disclosure relates generally to compositions comprising coated particles and to methods of making and using such compositions for targeted drug delivery.

Brief Description of Related Technology

Nanoparticles (including nanospheres) and microparticles (including microspheres) referred to herein collectively as "particles," are solid or semi-solid particles having a diameter from about 1 nm to about 10,000 nm (10 microns), preferably from about 1 nm to about 2,000 nm (2 microns). Such particles can be formed from a variety of materials, including proteins, synthetic polymers, polysaccharides, nucleic acids, small molecules, and combinations thereof, and have been used in many different applications, primarily separations, diagnostics, and drug delivery.

Compositions comprising such particles have been found to be useful for drug delivery. For example, U.S. Patent Publication No. 2006/0073199 discloses that particles comprising an active agent can be formulated as aqueous suspensions, and stabilized against aggregation and particle growth by providing surfactant coatings on or about the particles.

There is an on-going need for development of compositions comprising particles and methods for making and using same, particularly in delivering drugs of interest.

SUMMARY

One aspect of the invention is directed to a surface-modified particle comprising a particle core and a coating associated with the particle core. The particle core comprises an active agent, such as a therapeutic agent or a diagnostic agent (e.g., a small organic molecule or a biomacromolecule). The coating comprises a surfactant having formula I:

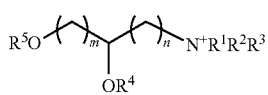

(I)

wherein n and m are independently selected from the group consisting of 1, 2, 3, 4, 5, and 6; $R^1$, $R^2$, and $R^3$ are independently selected from $C_1$ to $C_8$ alkyl; and $R^4$ and $R^5$ are independently selected from the group consisting of $C_6$ to $C_{40}$ alkyl, $C_6$ to $C_{40}$ alkenyl, $C_6$ to $C_{40}$ alkynyl, $C(=O)(C_5$ to $C_{39}$ alkyl), $C(=O)(C_5$ to $C_{39}$ alkenyl), and $C(=O)(C_5$ to $C_{39}$ alkenyl). The surface-modified particles according to the present invention generally have an average size from about 1 nm to about 2,000 nm.

Another aspect of the invention is directed to a method of enhancing cellular uptake of an active agent. The method comprises contacting cells with surface-modified particles under conditions sufficient to enhance cellular uptake of the surface-modified particles. The particles comprise a particle core and a coating associated with the particle core, wherein the particle core comprises an active agent, the coating comprises a surfactant of formula I, as defined herein, and the surface-modified particle has an average size from about 1 nm to about 2,000 nm.

Another aspect of the invention is directed to a method for treating a subject having an inflammatory disease or disorder comprising administering to said subject a plurality of surface-modified particles, said surface-modified particles comprising a particle core and a coating associated with the particle core, wherein the particle core comprises an active agent (e.g., an anti-inflammatory agent), the coating comprises a surfactant of formula I, as defined herein, the surface-modified particle has an average size from about 1 nm to about 2,000 nm, and said administration is effective in alleviating, treating, and/or preventing symptoms or pathologies associated with said inflammatory disease or disorder.

Another aspect of the invention is directed to a method for treating a subject having a proliferative disease or disorder comprising administering to said subject a plurality of surface-modified particles, said surface-modified particles comprising a particle core and a coating associated with the particle core, wherein the particle core comprises an active agent (e.g., an anti-proliferative such as an antineoplastic agent), the coating comprises a surfactant of formula I, as defined herein, the surface-modified particle has an average size from about 1 nm to about 2,000 nm, and said administration is effective in alleviating, treating, and/or preventing symptoms or pathologies associated with said proliferative disease or disorder.

Another aspect of the invention is directed to a method for treating a subject having an infectious disease or disorder comprising administering to said subject a plurality of surface-modified particles, said surface-modified particles comprising a particle core and a coating associated with the particle core, wherein the particle core comprises an active agent (e.g., an anti-infective agent), the coating comprises a surfactant of formula I, as defined herein, the surface-modified particle has an average size from about 1 nm to about 2,000 nm, and said administration is effective in alleviating, treating, and/or preventing symptoms or pathologies associated with said infectious disease or disorder.

In another aspect, the invention is directed to a method for treating a subject having a neurodegenerative disease or disorder comprising administering to said subject a plurality of surface-modified particles, said surface-modified particles comprising a particle core and a coating associated with the particle core, wherein the particle core comprises an active agent (e.g., an anti-neurodegenerative agent), the coating comprises a surfactant of formula I, as defined herein, the surface-modified particle has an average size from about 1 nm to about 2,000 nm, and said administration is effective in alleviating, treating, and/or preventing symptoms or pathologies associated with said neurodegenerative disease or disorder.

Another aspect of the invention is directed to a method for treating a subject having an infectious disease or disorder, an inflammatory disease or disorder, a neurodegenerative disease or disorder, or a proliferative disease or disorder comprising administering to said subject a plurality of surface-modified particles into a body cavity having a site of disease or inflammation, said surface-modified particles comprising a particle core and a coating associated with the particle core, wherein the particle core comprises an active agent, the coating comprises a surfactant of formula I, as defined herein, the surface-modified particle has an average size from about 1 nm to about 2,000 nm, and said administration is effective in alleviating, treating, and/or preventing symptoms or pathologies associated with said disease or disorder.

Each of the aforementioned methods for treating can be effected by using cellular transport to deliver the surface-modified particles to a target tissue of the subject, or by localized administration of the surface-modified particles into a body cavity having a site of disease (e.g., cancer, infection) and/or inflammation in the subject such that the surface-modified particles can be taken up by diseased or inflammatory cells located within the body cavity.

DETAILED DESCRIPTION

Figure 1A:
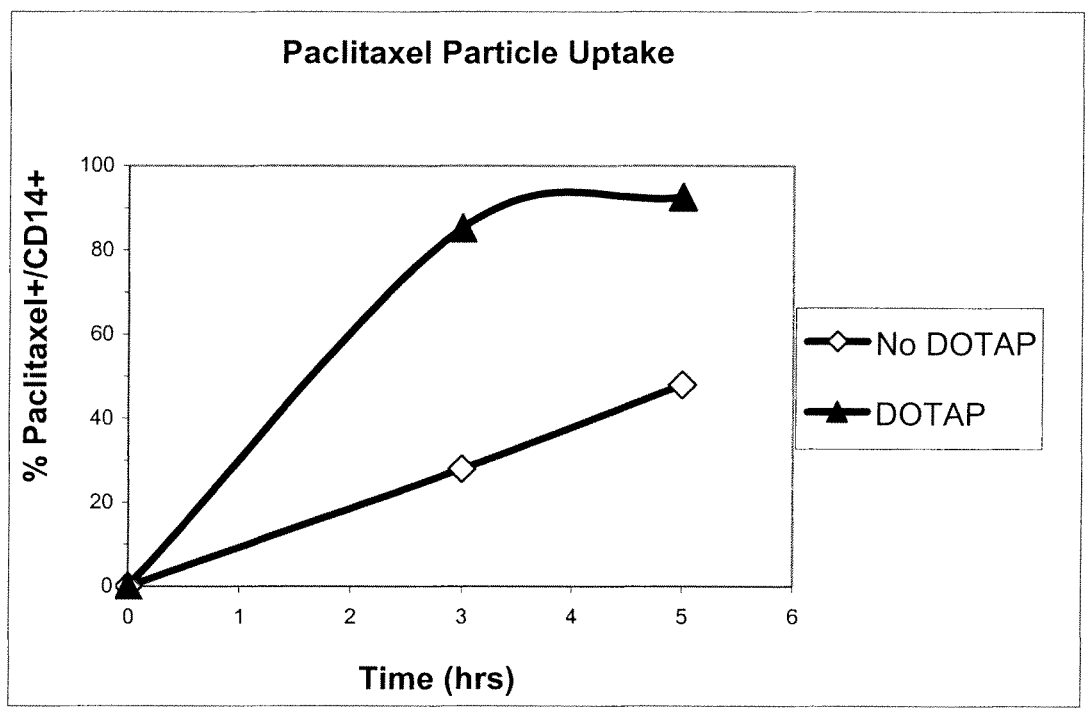
FIG. 1 provides graphs showing uptake of DSPE-mPEG2000/poloxamer 188-coated paclitaxel particles labeled with Oregon Green (No DOTAP) and DOTAP-coated paclitaxel particles labeled with Oregon Green (DOTAP).

The claimed invention is susceptible of embodiments in many different forms. Preferred embodiments, as disclosed herein, are to be considered exemplary of the principles of the claimed invention and thus not intended to limit the broad aspects of the claimed invention to the embodiments illustrated.

One aspect of the invention provides a surface-modified particle comprising a particle core and a coating associated with the particle core. The particle core comprises an active agent which is typically selected from the group consisting of small molecules, peptides, and proteins, the coating comprises a surfactant having formula I:

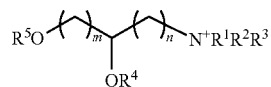

(I)

wherein n and m are independently selected from the group consisting of 1, 2, 3, 4, 5, and 6; $R^1$, $R^2$, and $R^3$ are independently selected from $C_1$ to $C_8$ alkyl; and $R^4$ and $R^5$ are independently selected from the group consisting of $C_6$ to $C_{40}$ alkyl, $C_6$ to $C_{40}$ alkenyl, $C_6$ to $C_{40}$ alkynyl, C(=O)($C_5$ to $C_{39}$ alkyl), C(=O)($C_5$ to $C_{39}$ alkenyl), and C(=O)($C_5$ to $C_{39}$ alkynyl), and the surface-modified particle has an average size from about 1 nm to about 2,000 nm.

As used herein, the term "alkyl" refers to straight chained and branched saturated hydrocarbon groups, nonlimiting examples of which include methyl, ethyl, and straight chain and branched propyl and butyl groups. Alkyl groups optionally can be substituted, for example, with one or more hydroxy (—OH), oxo (=O), halo (—F, —Cl, —Br, or —I), and thio (—SH) groups or a combination thereof.

As used herein, the term "alkenyl" refers to straight chained and branched hydrocarbon groups containing at least one carbon-carbon double bond, nonlimiting examples of which include straight chain and branched hexadecenyl and octadecenyl groups. Alkenyl groups optionally can be substituted, for example, with one or more hydroxy (—OH), oxo (=O), halo (—F, —Cl, —Br, or I), and thio (—SH) groups or a combination thereof.

As used herein, the term "alkynyl" refers to straight chained and branched hydrocarbon groups containing at least one carbon-carbon triple bond, nonlimiting examples of which include straight chain and branched hexadecynyl and octadecynyl groups. Alkynyl groups optionally can be substituted, for example, with one or more hydroxy (—OH), oxo (=O), halo (—F, —Cl, —Br, or I), and thio (—SH) groups or a combination thereof.

$R^1$, $R^2$, and $R^3$ alkyl groups of formula I can have, for example, from 1 to 8 carbon atoms, from 1 to 6 carbon atoms, and/or from 1 to 4 carbon atoms. In some embodiments, $R^1$, $R^2$, and $R^3$ are independently selected from the group consisting of methyl and ethyl.

$R^4$ and $R^5$ alkyl groups of formula I can have, for example, from 6 to 40 carbon atoms, from 10 to 24 carbon atoms, from 14 to 18 carbon atoms, from 5 to 39 carbon atoms, from 9 to 23 carbon atoms, and/or from 13 to 17 carbon atoms.

$R^4$ and $R^5$ alkenyl groups of formula I can have, for example, 1, 2, 3, 4, 5, 6, or more double bonds. The $R^4$ and $R^5$ alkenyl groups can have, for example, from 6 to 40 carbon atoms, from 10 to 24 carbon atoms, from 14 to 18 carbon atoms, from 5 to 39 carbon atoms, from 9 to 23 carbon atoms, and/or from 13 to 17 carbon atoms.

$R^4$ and $R^5$ alkynyl groups of formula I can have, for example, 1, 2, 3, 4, 5, 6, or more triple bonds. The $R^4$ and $R^5$ alkynyl groups can have, for example, from 6 to 40 carbon atoms, from 10 to 24 carbon atoms, from 14 to 18 carbon atoms, from 5 to 39 carbon atoms, from 9 to 23 carbon atoms, and/or from 13 to 17 carbon atoms.

In some embodiments, $R^4$ and $R^5$ are independently selected from the group consisting of octyl, 2-ethylhexyl, nonyl, decyl, dodecyl, tetradecyl, hexadecyl, cis-9-hexadecenyl, octadecyl, 16-methylheptadecyl, trans-9-octadecenyl, cis-9-octadecenyl, cis,cis-9,12-octadecadienyl, trans,trans-9,12-octadecadienyl, cis,cis,cis-9,12,15-octadecatrienyl, trans,trans,trans-9,12,15-octadecatrienyl, 12-hydroxy-9-octadecenyl, eicosanyl, docosanyl, cis-13-docosenyl, tetracosanyl, hexacosanyl, octacosanyl, triacontanyl, tetratriacontanyl, octanoyl, decanoyl, dodecanoyl, tetradecanoyl, hexadecanoyl, heptadecanoyl, octadecanoyl, eicosanoyl, docosanoyl, tetracosanoyl, cis,cis,cis-9,12,15-octadecatrienoyl, cis,cis,cis-6,9,12,15-octadecatetraenoyl, cis,cis,cis,cis-5,8,11,14,17-eicosapentenoyl, cis,cis,cis,cis,cis, cis-4,7,10,13,16,19-docosahexaenoyl, cis,cis-9,12-octadecadienoyl, cis,cis,cis-6,9,12-octadecatrienoyl, cis,cis,cis-8,11,14-eicosatrienoyl, cis,cis,cis,cis-5,8,11,14-eicosatetraenoyl, cis-9-octadecenoyl, trans-9-octadecenoyl, cis-13-docosenoyl, and cis-15-tetracosenoyl.

In some embodiments, m and n are 1; $R^1$, $R^2$, and $R^3$ are methyl; and $R^4$ and $R^5$ are cis-9-octadecenoyl, i.e., the surfactant of formula I is N-[1-(2,3-dioleoyloxy)propyl]-N,N,N-trimethylammonium (DOTAP) or a salt thereof. In other embodiments, m and n are 1; $R^1$, $R^2$, and $R^3$ are methyl; and $R^4$ and $R^5$ are cis-9-octadecenyl, i.e., the surfactant of formula I is N-[1-(2,3-dioleyloxy)propyl]-N,N,N-trimethylammonium (DOTMA), or a salt thereof. In some embodiments, the active agent is paclitaxel; m and n are 1; $R^1$, $R^2$, and $R^3$ are methyl; and $R^4$ and $R^5$ are cis-9-octadecenoyl, i.e., the surfactant of formula I is N-[1-(2,3-dioleoyloxy)propyl]-N,N,N-trimethylammonium (DOTAP) or a salt thereof. In other embodiments, the active agent is paclitaxel; m and n are 1; $R^1$, $R^2$, and $R^3$ are methyl; and $R^4$ and $R^5$ are cis-9-octadecenyl, i.e., the surfactant of formula I is N-[1-(2,3-dioleyloxy)propyl]-N,N,N-trimethylammonium (DOTMA), or a salt thereof.

Another aspect of the present invention provides methods for enhancing uptake of an active agent by phagocytic or non-phagocytic cells by exposing the cells to a surface-modified particle comprising a particle core and a coating associated with the particle core, thereby forming cells loaded with the surface modified particles. The particle core comprises an active agent which is typically selected from the group consisting of small molecules, peptides, and proteins, the coating comprises a surfactant of formula I, as defined herein, and the surface-modified particle has an average size from about 1 nm to about 2,000 nm. Enhanced uptake by the cells of the active agent is observed at least as compared to cells contacted with particles not having a coating comprising a surfactant of formula I. Such methods can be performed in vivo or ex vivo to form cells loaded with the surface modified particles. In yet another aspect, the invention also provides methods for delivery of a surface-modified particle to a target tissue of a mammalian subject through cellular transport using the aforementioned cells loaded with the surface modified particles. It is contemplated that various methods of administration, such as intravenous administration, intramuscular administration, subcutaneous administration, and the like will facilitate enhanced uptake of particles by cells that traffic to the lymphatic system, the liver, and other tissue targets. Subcutaneous administration, for example, is contemplated for various diseases, including head and neck cancers which invade locoregionally along the lymphatics.

As used herein, "target tissue" or "tissue target" refers to the particular tissue of the subject to be treated. Examples of such target tissues include, but are not limited to, the brain and other portions of the central nervous system, the lymphatic system (e.g., lymph nodes, bone marrow, spleen, thymus, etc.), the liver, and any site of infection, inflammation, or tumor.

In addition to delivery by cellular transport, delivery to a target tissue can be effected by localized administration of the surface-modified particles into a body cavity having a site of disease (e.g., cancer, infection) and/or inflammation in the subject such that the surface-modified particles can be taken up by diseased or inflammatory cells located within the body cavity so as to deliver the active agent in close proximity to the diseased tissue target. For example, cancers of the peritoneal cavity such as ovarian cancer, peritoneal mesothelioma, peritoneal carcinomatosis, and the like can be treated by intraperitoneally administering the particles into the peritoneal cavity. Similarly, bladder cancers, infections, and/or inflammation can be treated by administering the particles into the bladder cavity; pulmonary cancers, infections, and/or inflammation can be treated by administering the particles into the pulmonary cavity (e.g., via inhalation); cancers, infections, and/or inflammation of the pleural cavity can be treated by administering particles into the pleural cavity; cancers, infections, and/or inflammation of the cardiac cavity can be treated by administering particles into the cardiac cavity; and ophthalmic cancers, infections, and/or inflammation can be treated by administering the particles into the aqueous humor or vitreous humor of the eye. Advantageously, when the surface-modified particles are administered proximate to and/or adjacent to a site of disease or inflammation via administration to a body cavity containing the site of disease or inflammation, the surface-modified particles can be taken up by the diseased (e.g., cancerous, infected) or inflammatory cells located at the site of disease or inflammation such that enhanced uptake by the diseased or inflammatory cells of the surface modified particles according to the invention is observed at least as compared to cells contacted with particles not having a coating comprising a surfactant of formula I.

As used herein, a "body cavity" refers to a relatively empty space surrounded by a supporting tissue or a fluid-filled space surrounded by a supporting tissue. As used herein, a body cavity encompasses both the tissue surrounding (and defining) the cavity and the complete interior of the cavity. Exemplary body cavities include the peritoneal cavity, the bladder cavity, the pulmonary cavity, the pleural cavity, the cardiac cavity, the aqueous humor of the eye, and the vitreous humor of the eye.

In one aspect, the invention contemplates methods and compositions for treating a subject having an inflammatory disease or disorder comprising administering to said subject a plurality of surface-modified particles, said surface-modified particles comprising a particle core and a coating associated with the particle core, wherein the particle core comprises an active agent which is typically selected from the group consisting of small molecules, peptides, and proteins, the coating comprises a surfactant of formula I, as defined herein, the surface-modified particle has an average size from about 1 nm to about 2,000 nm, and said administration is effective in alleviating, treating, and/or preventing symptoms or pathologies associated with said inflammatory disease or disorder. In one aspect, the subject has an inflammatory disease or disorder, and m and n are 1; $R^1$, $R^2$, and $R^3$ are methyl; and $R^4$ and $R^5$ are cis-9-octadecenoyl. In one aspect, the active agent is an anti-inflammatory agent. Delivery of the active agent can be effected via cellular transport, as described herein, or by local administration to the site of inflammation, as described herein.

In another aspect, the invention contemplates methods and compositions for treating a subject having a neurodegenerative disease or disorder comprising administering to said subject a plurality of surface-modified particles, said surface-modified particles comprising a particle core and a coating associated with the particle core, wherein the particle core comprises an active agent which is typically selected from the group consisting of small molecules, peptides, and proteins, the coating comprises a surfactant of formula I, as defined herein, the surface-modified particle has an average size from about 1 nm to about 2,000 nm, and said administration is effective in alleviating, treating, and/or preventing symptoms or pathologies associated with said neurodegenerative disease or disorder. In one aspect, the subject has a neurodegenerative disease or disorder, and m and n are 1; $R^1$, $R^2$, and $R^3$ are methyl; and $R^4$ and $R^5$ are cis-9-octadecenoyl. In one aspect, the active agent is an anti-neurodegenerative agent. Delivery of the active agent can be effected via cellular transport, as described herein.

In yet another aspect, the invention contemplates methods and compositions for treating a subject having a proliferative disease or disorder comprising administering to said subject a plurality of surface-modified particles, said surface-modified particles comprising a particle core and a coating associated with the particle core, wherein the particle core comprises an active agent which is typically selected from the group consisting of small molecules, peptides, and proteins, the coating comprises a surfactant of formula I, as defined herein, the surface-modified particle has an average size from about 1 nm to about 2,000 nm, and said administration is effective in alleviating, treating, and/or preventing symptoms or pathologies associated with said proliferative disease or disorder. In one aspect, the subject has a proliferative disease or disorder, and m and n are 1; $R^1$, $R^2$, and $R^3$ are methyl; and $R^4$ and $R^5$ are cis-9-octadecenoyl. In one aspect, the active agent is an anti-proliferative agent such as an antineoplastic agent. Delivery of the active agent can be effected via cellular transport, as described herein, or by local administration to the site of disease, as described herein.

In a still further aspect, the invention contemplates methods and compositions for treating a subject having an infectious disease or disorder comprising administering to said subject a plurality of surface-modified particles, said surface-modified particles comprising a particle core and a coating associated with the particle core, wherein the particle core comprises an active agent which is typically selected from the group consisting of small molecules, peptides, and proteins, the coating comprises a surfactant of formula I, as defined herein, the surface-modified particle has an average size from about 1 nm to about 2,000 nm, and said administration is effective in alleviating, treating, and/or preventing symptoms or pathologies associated with said infectious disease or disorder. In one aspect, the subject has an infectious disease or disorder, and m and n are 1; $R^1$, $R^2$, and $R^3$ are methyl; and $R^4$ and $R^5$ are cis-9-octadecenoyl. In one aspect, the active agent is an anti-infective agent such as an anti-fungal agent, an anti-viral agent, an anti-bacterial agent, or an anti-parasitic agent. Delivery of the active agent can be effected via cellular transport, as described herein, or by local administration to the site of disease, as described herein.

Thus, the methods of administration disclosed herein contemplate administration of a therapeutically effective amount of said surface modified particles. As used herein, the term "therapeutically effective amount" refers to an amount of surface-coated particles that is sufficient to alleviate, ameliorate, clear, treat, and/or prevent symptoms or pathologies associated with a disease or disorder contemplated for treatment in accordance with the treatment methods disclosed herein. Determination of therapeutically effective amounts is well within the capability of those skilled in the art, especially in light of the disclosure provided herein.

The following description of the surface-modified particle applies to all embodiments disclosed herein. The active agent of the surface-modified particle can be poorly water soluble or water soluble. The active agent can be a therapeutic agent or a diagnostic agent. The active agent can be a small molecule or a biologic, such as a protein, a peptide, a carbohydrate, or a complex, conjugate, or combination thereof. In one preferred aspect, DNA, RNA, oligonucleotides, and polynucleotides are not suitable active agents for use with the surface modified particles of the invention. Active agents used in accordance with the compositions and methods disclosed herein exhibit the pharmaceutical activities normally associated with such active agents notwithstanding that the active agents can be taken up and subsequently delivered to target tissues by phagocytic or non-phagocytic cells. As discussed above, active agents also can be administered locally at a site of disease (e.g., cancer, infection) and/or inflammation in a mammalian subject and taken up by diseased cells (such as infected or cancerous cells), or inflammatory cells, located at the site of disease and/or inflammation.

The active agent can be selected from a variety of known pharmaceutical compounds such as, but not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, anticoagulants, antidepressants, antiepileptics, antifibrotic agents, anti-infective agents (e.g., antifungals, antiviral agents such as antiretroviral agents, and antibiotics), antihistamines, antimuscarinic agents, antimycobacterial agents, antineoplastic agents, antiprotozoal agents, anxiolytic sedatives, beta-adrenoceptor blocking agents, corticosteroids, cough suppressants, dopaminergics, hemostatics, hematological agents, hypnotics, immunological agents, muscarinics, parasympathomimetics, prostaglandins, radio-pharmaceuticals, sedatives, stimulants, sympathomimetics, vitamins, xanthines, growth factors, hormones, and antiprion agents.

Examples of antineoplastic agents include, but are not limited to, paclitaxel, paclitaxel derivative compounds, alkaloids, antimetabolites, enzyme inhibitors, alkylating agents, and combinations thereof.

The active agent also can be a protease inhibitor, such as an HIV protease inhibitor. Examples of protease inhibitors include, but are not limited to, indinavir, ritonavir, saquinavir, nelfinavir, and combinations thereof.

The active agent can be a nucleoside reverse transcriptase inhibitor. Examples of nucleoside reverse transcriptase inhibitors include, but are not limited to, zidovudine, didanosine, stavudine, zalcitabine, lamivudine, and combinations thereof.

The active agent can be a non-nucleoside reverse transcriptase inhibitor. Examples of non-nucleoside reverse transcriptase inhibitors include, but are not limited to, efavirenz, nevirapine, delaviradine, and combinations thereof.

Examples of anti-inflammatory agents include, but are not limited to, non-steroidal anti-inflammatory drugs, non-selective cycloxygenase (COX) inhibitors, COX-1 inhibitors, COX-2 inhibitors, lipoxygenase inhibitors, corticosteroids, anti-oxidants, tumor necrosis factor (TNF) inhibitors, and combinations thereof. Examples of COX-2 inhibitors include, but are not limited to, celecoxib, rofecoxib, valdecoxib, parecoxib, lumiracoxib, etoricoxib, and combinations thereof.

Diagnostic agents include x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodo-benzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy)acetamide (WIN 12855); diethyl 2-(3,5-bis(acetamido)-2,4,6-triiodobenzoyloxy) malonate (WIN 67721); ethyl 2-(3,5-bis(acetamido)-2,4,6-triiodobenzoyloxy)phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triiodo-4-(ethyl-3-ethoxy-2-butenoate) ester (WIN 68209). Contrast agents include those that are expected to disintegrate relatively rapidly under physiological conditions, thus minimizing any particle associated inflammatory response. Disintegration can result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 are included.

Other contrast media include, but are not limited to, particulate preparations of magnetic resonance imaging aids such as gadolinium chelates, or other paramagnetic contrast agents. Examples of such compounds are gadopentetate dimeglumine (MAGNEVIST®) and gadoteridol (PROHANCE®).

A description of classes of therapeutic agents and diagnostic agents and a listing of species within each class can be found in Martindale, The Extra Pharmacopoeia, 31 st Edition, The Pharmaceutical Press, London, 1996 which is incorporated herein by reference and made a part hereof. The listed therapeutic agents and diagnostic agents are commercially available and/or can be prepared by known techniques.

In a specific embodiment, the active agent is a poorly water-soluble compound. What is meant by "poorly water soluble" is a solubility of the compound in water of less than about 10 mg/mL, and preferably less than about 1 mg/mL. These poorly water-soluble compounds are particularly suitable for aqueous suspension preparations since there are limited alternatives of formulating these compounds in an aqueous medium. Advantageously, surfactants of formula I, which provide the coatings in accordance with the invention, can adsorb to the surface of particles comprising such poorly water soluble active agents to form a substantially uniform coating thereon. For example, the hydrophobic tail moieties of surfactants of formula I can associate with hydrophobic regions on the particle surface. In addition, surfactants of formula I are positively charged, and thus electrostatic interactions between the surfactant and negatively charged regions on the particle surface can stabilize the coating comprising the surfactant of formula I. In one preferred aspect, the poorly water soluble active agent compound is an organic compound having a molecular weight less than 2500 grams/mol, less than 2000 grams/mol, and most typically less than 1000 grams/mol, for example, between 200 grams/mol and 900 grams/mol. Such organic compounds are referred to herein as "small molecules."

Alternatively, the invention can be practiced with water-soluble compounds. To form aqueous suspensions of water-soluble compounds the water soluble active compounds can be entrapped in a solid carrier matrix (for example, polylactate-polyglycolate copolymer, albumin, starch), or encapsulated in a surrounding vesicle that is substantially impermeable to the active agent. This encapsulating vesicle can be a polymeric coating such as polyacrylate. Further, the small particles prepared from these water soluble compounds can be modified to improve chemical stability and control the pharmacokinetic properties of the compounds by controlling the release of the compounds from the particles. Examples of water-soluble compounds include, but are not limited to, simple organic compounds, proteins, peptides, nucleotides, and carbohydrates.

The following description of particles also applies to all embodiments disclosed herein. The particles can be amorphous, semicrystalline, crystalline, or a combination thereof as determined by suitable analytical methods such as differential scanning calorimetry (DSC) or X-ray diffraction. Prior to administration, the particles can be homogenized through a homogenization process. The particles can also be homogenized through a microprecipitation/homogenization process.

The coated particles generally have an average effective particle size of generally from about 1 nm to about 2 µm (or 2000 nanometers) as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), rheology, or microscopy (light or electron). The preferred average effective particle size depends on factors such as the intended route of administration, formulation, solubility, toxicity and bioavailability of the compound. Other suitable particle sizes include, but are not limited to, about 10 nm to about 1 µm, about 50 nm to about 500 nm, and/or about 100 nm to about 250 nm.

In all embodiments, the coated particles are solid or semi-solid particles comprising active agents. The coated particles generally consist of at least 5% (w/w) active agent, for example, at least 10% (w/w), at least 25% (w/w), at least 50% (w/w), and/or at least 75% (w/w) or more active agent.

Preparation of the Particle Core

The processes for preparing the particles used in the present invention can be accomplished through numerous techniques. A representative, but non-exhaustive, discussion of techniques for preparing particles follows.

I. Energy Addition Techniques for Forming Small Particle Dispersions

In general, the method of preparing small particle dispersions using energy addition techniques includes the step of adding the active agent or pharmaceutically active compound, which sometimes shall be referred to as a drug, in bulk form to a suitable vehicle such as water or aqueous solution generally containing one or more of the surfactants set forth below, other liquid in which the pharmaceutical compound is not appreciably soluble, to form a first suspension, which shall be referred to as a presuspension. Energy is added to the presuspension to form a particle dispersion which is physically more stable than the presuspension. Energy is added by mechanical grinding (e.g., pearl milling, ball milling, hammer milling, fluid energy milling, jet milling, or wet grinding). Such techniques are disclosed in U.S. Pat. No. 5,145,684, which is incorporated herein by reference and made a part hereof.

Energy addition techniques further include subjecting the presuspension to high shear conditions including cavitation, shearing or impact forces utilizing a microfluidizer. The present invention further contemplates adding energy to the presuspension using a piston gap homogenizer or counter current flow homogenizer such as those disclosed in U.S. Pat. No. 5,091,188 which is incorporated herein by reference and made a part hereof. Suitable piston gap homogenizers are commercially available under the product names EMUL- SIFLEX™ (Avestin) and FRENCH® Pressure Cell (Thermo Spectronic). Suitable microfluidizers are available from Microfluidics Corp.

The step of adding energy can also be accomplished using sonication techniques. The step of sonicating can be carried out with any suitable sonication device. Suitable devices include Branson Model S-450A and Cole-Parmer 500/750 Watt Model. Such devices are well known in the industry. Typically the sonication device has a sonication horn or probe that is inserted into the presuspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably are in distinct sizes such as ½ inch or ¼ inch or the like.

The dispersion of small particles can be sterilized prior to administering. Sterilization can be accomplished by heat sterilization, gamma irradiation, filtration (either directly as a dispersion having particle sizes under 200 nm, or by sterile filtration of the solutions used in the precipitation process, prior to forming the solid dispersion), and by application of very high pressure (greater than 2000 atmospheres), or by a combination of high pressure and elevated temperature.

II. Precipitation Methods for Preparing Submicron Sized Particle Dispersions

Small particle dispersions can also be prepared by precipitation techniques. The following is a description of examples of precipitation techniques.

Microprecipitation Methods. One example of a microprecipitation method is disclosed in U.S. Pat. No. 5,780,062, which is incorporated herein by reference and made a part hereof. The '062 patent discloses an organic compound precipitation process including: (i) dissolving the organic compound in a water-miscible first solvent; (ii) preparing a solution of polymer and an amphiphile in an aqueous second solvent and in which second solvent the organic compound is substantially insoluble whereby a polymer/amphiphile complex is formed; and (iii) mixing the solutions from steps (i) and (ii) so as to cause precipitation of an aggregate of the organic compound and the polymer/amphiphile complex.

Other suitable precipitation processes are disclosed in U.S. Pat. Nos. 6,607,784, 7,037,528, 6,869,617, 6,884,436, which are incorporated herein by reference and made a part hereof. The processes disclosed include the steps of: (1) dissolving an organic compound in a water miscible first organic solvent to create a first solution; (2) mixing the first solution with a second solvent or water to precipitate the organic compound to create a presuspension; and (3) adding energy to the presuspension in the form of high-shear mixing or heat to provide a dispersion of small particles. Optionally, the first organic solvent is removed from the mixture by any suitable means such as centrifugation or filtration methods. Moreover, the continuous phase of the dispersion can be optionally replaced by another continuous phase by removing the first continuous phase using methods such as centrifugation and filtration, and adding a second continuous phase and subsequently redispersing the solid material in the second continuous phase. One or more optional surfactants set forth below can be added to the first organic solvent, to the second aqueous solution, or to both the first organic solvent and the second aqueous solution.

Emulsion Precipitation Methods. One suitable emulsion precipitation technique is disclosed in U.S. Patent Pub. No. 2005/0037083, which is incorporated herein by reference and is made a part hereof. In this approach, the process includes the steps of: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 µm in diameter. The crude emulsion is sonicated to define a microemulsion and eventually to provide a dispersion of small particles.

Another approach to preparing a dispersion of small particles is disclosed U.S. Pat. No. 6,835,396, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth below or the small particles can be reconstituted in an aqueous medium and sterilized.

The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent-Antisolvent Precipitation. Small particle dispersions can also be prepared using a solvent-antisolvent precipitation technique disclosed by Fessi et al. in U.S. Pat. No. 5,118,528 and by Leclef et al. in U.S. Pat. No. 5,100,591 which are incorporated herein by reference and made a part hereof. Both processes include the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles. These methods are distinguished from those described under the above section, "Microprecipitation Methods", in that they do not provide for a last step of adding energy to the suspension in the form of high-shear mixing or heat.

Phase Inversion Precipitation. Small particle dispersions can be formed using phase inversion precipitation as disclosed in U.S. Pat. Nos. 6,235,224, 6,143,211 and 6,616, 869, each of which is incorporated herein by reference and made a part hereof. Phase inversion is a term used to describe the physical phenomena by which a polymer dissolved in a continuous phase solvent system inverts into a solid macromolecular network in which the polymer is the continuous phase. One method to induce phase inversion is by the addition of a nonsolvent to the continuous phase. The polymer undergoes a transition from a single phase to an unstable two phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process, it is desirable the agent is dissolved in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 µm. The particle size is influenced by the solvent:nonsolvent volume ratio, polymer concentration, the viscosity of the polymer-solvent solution, the molecular weight of the polymer, and the characteristics of the solvent-nonsolvent pair.

pH Shift Precipitation. Small particle dispersions can be formed by pH shift precipitation techniques. Such techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a dispersion of small particles. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a small particle dispersion of the pharmaceutical agent. The precipitation step can be followed by steps of diafiltration clean-up of the dispersion and then adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method. Suitable infusion precipitation techniques to form small particle dispersions are disclosed in U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 µm. Agitation (e.g., by stirring) of the solution being infused with the precipitating nonsolvent is preferred. The nonsolvent may contain a surfactant to stabilize the particles against aggregation. The particles are then separated from the solvent. Depending on the solid compound and the desired particle size, the parameters of temperature, ratio of nonsolvent to solvent, infusion rate, stir rate, and volume can be varied according to the invention. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation. Temperature shift precipitation techniques may also be used to form small particle dispersions. This technique is disclosed in U.S. Pat. No. 5,188,837, which is incorporated herein by reference and made a part hereof. In an embodiment of the invention, liposheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation. Solvent evaporation precipitation techniques are disclosed in U.S. Pat. No. 4,973,465 which is incorporated herein by reference and made a part hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring to form a dispersion of small particles. The solvent can be removed by evaporating a sufficient quantity of the solvent to cause precipitation of the compound. The solvent can also be removed by other well known techniques such as applying a vacuum to the solution or blowing nitrogen over the solution.

Reaction Precipitation. Reaction precipitation includes the steps of dissolving the pharmaceutical compound, and optionally other excipients, into a suitable solvent to form a solution. The compound may be added in an amount at or below the saturation point of the compound in the solvent. The compound or any of the excipients is precipitated from solution by reacting with a chemical agent or by modification in response to adding energy such as heat or UV light or the like such that the modified compound has a lower solubility in the solvent and precipitates from the solution to form a small particle dispersion. Precipitation of excipient provides a solid matrix into which the drug is sorbed.

Compressed Fluid Precipitation. A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an antisolvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent.

In order to stabilize the particles against aggregation, a surface modifier, such as a surfactant, is included in this technique.

Spraying into Cryogenic Fluids. A suitable technique for precipitating by compressed fluid is disclosed by Williams et al. in U.S. Patent Pub. No. 2004/0022861, which is incorporated herein by reference and made a part hereof. The method provides a system and method for the production of small particles wherein the active ingredient is mixed with water, one or more solvents, or a combination thereof, and the resulting mixture sprayed at or below the surface of a cryogenic fluid. Frozen particles are thereby provided. Materials for encapsulating the solid particles may also be added so that frozen particles are generated wherein the encapsulating agent surrounds the active agent.

Protein Nanosphere/Microsphere Precipitation. Particles utilized in this invention can also be produced from a process involving mixing or dissolving macromolecules such as proteins with a water soluble polymer. This process is disclosed in U.S. Pat. Nos. 5,981,719, 6,090,925, 6,268,053, 6,458,387, and U.S. Patent Pub. No. 2004/0043077, which are incorporated herein by reference and made a part hereof. In an embodiment of the invention, particles are prepared by mixing a macromolecule in solution with a polymer or a mixture of polymers in solution at a pH near the isoelectric point of the macromolecule. The mixture is incubated in the presence of an energy source, such as heat, radiation, or ionization, for a predetermined amount of time. The resulting particles can be removed from any unincorporated components present in the solution by physical separation methods.

There are numerous other suitable methodologies for preparing small particle dispersions capable of use in accordance with the invention.

III. Additional Methods for Preparing Particle Dispersions of Pharmaceutical Compositions The following additional processes for preparing particles of pharmaceutical compositions (i.e. active agent or organic compound) used in the present invention can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the presuspension in the form of high-shear mixing or heat, or a combination of both, to provide a stable form of the organic compound having desired size ranges defined above. The mixing steps and the adding energy step can be carried out in consecutive steps or simultaneously.

The categories of processes are distinguished based upon the physical properties of the organic compound as determined through x-ray diffraction studies, differential scanning calorimetry (DSC) studies, or other suitable study conducted prior to the energy-addition step and after the energy-addition step. In the first process category, prior to the energy-addition step the organic compound in the presuspension takes an amorphous form, a semi-crystalline form or a supercooled liquid form and has an average effective particle size. After the energy-addition step the organic compound is in a crystalline form having an average effective particle size essentially the same or less than that of the presuspension.

In the second process category, prior to the energy-addition step the organic compound is in a crystalline form and has an average effective particle size. After the energy-addition step, the organic compound is in a crystalline form having essentially the same average effective particle size as prior to the energy-addition step but the crystals after the energy-addition step are less likely to aggregate or form large crystals.

The lower tendency of the organic compound to aggregate or form large crystals is observed by laser dynamic light scattering and light microscopy.

In the third process category, prior to the energy-addition step the organic compound is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

In the fourth process category, the first solution and second solvent are simultaneously subjected to the energy-addition step. Thus, the physical properties of the organic compound before and after the energy addition step were not measured.

The energy-addition step can be carried out in any fashion wherein the presuspension or the first solution and second solvent are exposed to cavitation, shearing or impact forces. In one form, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These four process categories are shown separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

The first process category, as well as the second, third, and fourth process categories, can be further divided into two subcategories, Method A and B.

The first solvent according to the following processes is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997): a solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Other specific examples of solvents suitable for use as the first solvent include, but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, monoacylated and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, surfactant(s), water-soluble polymers, and combinations of these excipients.

Method A. In Method A, the organic compound ("active agent" or "drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with one or more optional surface modifiers such as an anionic surfactant, a cationic surfactant, a zwitterionic surfactant, a nonionic surfactant or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated, or natural, semisynthetic, or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecular weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

Suitable cationic surfactants include but are not limited to quaternary ammonium compounds, such as benzalkonium chloride, cetyltrimethylammonium bromide, chitosans, lauryldimethylbenzylammonium chloride, acyl carnitine hydrochlorides, dimethyldioctadecylammonium bromide (DDAB), dioleoyltrimethylammonium propane (DOTAP, also known as N-[1-(2,3-dioleoyloxy)propyl]-N,N,N-trimethylammonium), N-[1-(2,3-dioleyloxy)propyl]-N,N,N-trimethylammonium (DOTMA), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, or long-chain alkyl amines such as, for example, n-octylamine and oleylamine. Surfactants of formula I, as defined herein, also are suitable cationic surfactants.

Suitable nonionic surfactants include: glyceryl esters, polyoxyethylene fatty alcohol ethers (MACROGOL™ and BRIJ™), polyoxyethylene sorbitan fatty acid esters (polysorbates), polyoxyethylene fatty acid esters (MYRJ™), sorbitan esters (SPAN™), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form, the nonionic surfactant is a polyoxyethylene and polyoxypropylene copolymer and preferably a block copolymer of propylene glycol and ethylene glycol. Such polymers are sold under the trade name POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface-active biological molecules include such molecules as albumin, casein, hirudin or other appropriate proteins. For example, proteins having hydrophilic and hydrophobic domains also can be used. Polysaccharide surface active biologics are also included, and consist of but are not limited to, starches, heparins, and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

It may also be desirable to add a pH adjusting agent to the second solvent. Suitable pH adjusting agents include, but are not limited to, hydrochloric acid, sulfuric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The second solvent should have a pH within the range of from about 3 to about 11. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

For oral dosage forms, one or more of the following excipients may be utilized: gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENS™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

In a preferred form, the method for preparing small particles of an organic compound includes the steps of adding the first solution to the second solvent. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an energy-addition step to convert the amorphous particles, supercooled liquid or semicrystalline solid to a more stable, crystalline solid state. The resulting particles will have an average effective particles size as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), rheology, or microscopy (light or electron) within the ranges set forth above. In process category four, the first solution and the second solvent are combined while simultaneously conducting the energy-addition step.

The energy-addition step involves adding energy through sonication, homogenization, countercurrent flow homogenization, microfluidization, or other methods of providing impact, shear or cavitation forces. The sample may be cooled or heated during this stage. In one form, the energy-addition step is effected by a piston gap homogenizer such as the one sold by Avestin Inc. under the product designation EmulsiFlex-C160. In another form, the energy-addition step is accomplished by ultrasonication using an ultrasonic processor such as the Vibra-Cell Ultrasonic Processor (600W), manufactured by Sonics and Materials, Inc. In yet another form, the energy-addition step is accomplished by use of an emulsification apparatus as described in U.S. Pat. No. 5,720,551, which is incorporated herein by reference and made a part hereof.

Depending upon the rate of energy addition, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the energy-addition step.

Method B. Method B differs from Method A in the following respects. The first difference is a surfactant or combination of surfactants is added to the first solution. The surfactants may be selected from the groups of anionic, nonionic, cationic surfactants, and surface-active biological modifiers set forth above.

Comparative Example of Method A and Method B and U.S. Pat. No. 5,780,062. U.S. Pat. No. 5,780,062 discloses a process for preparing small particles of an organic compound by first dissolving the compound in a suitable water-miscible first solvent. A second solution is prepared by dissolving a polymer and an amphiphile in aqueous solvent. The first solution is then added to the second solution to form a precipitate that consists of the organic compound and a polymer-amphiphile complex. The '062 patent does not disclose utilizing the energy-addition step of this process in Methods A and B. Lack of stability is typically evidenced by rapid aggregation and particle growth. In some instances, amorphous particles recrystallize as large crystals. Adding energy to the pre-suspension in the manner disclosed above typically affords particles that show decreased rates of particle aggregation and growth, as well as the absence of recrystallization upon product storage.

Methods A and B are further distinguished from the process of the '062 patent by the absence of a step of forming a polymer-amphiphile complex prior to precipitation. In Method A, such a complex cannot be formed as no polymer is added to the diluent (aqueous) phase. In Method B, the surfactant, which may also act as an amphiphile, or polymer, is dissolved with the organic compound in the first solvent. This precludes the formation of any amphiphile-polymer complexes prior to precipitation. In the '062 patent, successful precipitation of small particles relies upon the formation of an amphiphile-polymer complex prior to precipitation. The '062 patent discloses the amphiphile-polymer complex forms aggregates in the aqueous second solution. The '062 patent explains the hydrophobic organic compound interacts with the amphiphile-polymer complex, thereby reducing solubility of these aggregates and causing precipitation. In the present process, it has been demonstrated that the inclusion of the surfactant or polymer in the first solvent (Method B) leads, upon subsequent addition to second solvent, to formation of a more uniform, finer particulate than is afforded by the process outlined by the '062 patent.

Coating of the Particles

The processes for coating the particles prepared by the present invention can be accomplished through various techniques known to those skilled in the art. The coating can be associated with the particle through various associations, including covalent and/or non-covalent associations (e.g., covalent bonding, ionic interactions, electrostatic interactions, dipole-dipole interactions, hydrogen bonding, van der Waal's forces, hydrophobic/hydrophobic domain interactions, cross-linking, and/or any other interactions).

Non-covalently bound coatings can be prepared, for example, by the methods for preparing particle cores disclosed herein provided that a surfactant according to formula I is used to manufacture the particles, or by mixing a plurality of pre-fabricated particles with a solution comprising a surfactant of formula I, as defined herein, to form surface-modified particles according to the invention. The solution can be mixed under high-shear conditions using, for example, a microfluidizer, a piston gap homogenizer, a counter-current flow homogenizer, or an ultrasonic processor. To confirm the coating successfully adsorbs to the particles, the surface electrical potential of the particles can be determined by measuring the zeta potential before and after the coating process. Other known methods for measuring the adsorption of coatings also can be used, for example, the surfactant of formula I can be modified with a fluorescent label and absorption of the fluorescently-labeled surfactant of formula I can be detected by fluorescence microscopy. Advantageously, the coatings comprising a surfactant of formula I can associate with the particle core, for example by adsorbing to the surface of particles, which is an efficient method for associating coatings comprising surfactants according to formula I to particle cores, particularly particles comprising poorly water soluble active agents, as explained above.

The coating can further include one or more additional surfactants, including additional surfactants of formula I, by adding the additional surfactants to the solution comprising the surfactant of formula I, as defined herein, and then mixing the pre-fabricated particles with said solution. Such additional surfactant(s) can be selected from a variety of known anionic surfactants, cationic surfactants, zwitterionic surfactants, nonionic surfactants and surface active biological modifiers. Suitable additional surfactants include the surfactants previously set forth herein. Exemplary additional surfactants include, but are not limited to, poloxamers, phospholipids, polyethylene glycol-conjugated phospholipids, and polysorbates. Exemplary combinations of additional surfactants include, but are not limited to, poloxamers and phospholipids, poloxamers and polyethylene glycol-conjugated phospholipids, and poloxamers and polysorbates.

Cellular Uptake of Coated Particles

One embodiment of the present invention is directed to a method of enhancing cellular uptake of an active agent, comprising contacting cells with a plurality of surface-modified particles, said particles comprising a particle core and a coating associated with the particle core. The cells can be phagocytic cells, weakly phagocytic cells, or non-phagocytic cells. The particle core comprises an active agent which is typically selected from the group consisting of small molecules, peptides, and proteins, the coating comprises a surfactant of formula I, as defined herein, and the surface-modified particle has an average size from about 1 nm to about 2,000 n. Uptake of the active agent by the cells is thereby enhanced, at least relative to the uptake of active agent when particles that do not comprise the aforementioned coating are used.

Uptake by cells allows the active agent to be delivered to target tissues in need of treatment because the various cell types capable of enhanced uptake of the coated particles in accordance with the disclosure also traffic to diseased (e.g., cancerous, infected) or inflamed tissues. For example, neutrophils predominate early in infection or inflammation, followed by monocyte-derived phagocytes that leave the blood vasculature and enter infected tissues, and such cells demonstrate enhanced uptake of the surface-modified particles according to the invention at least relative to particles not having a coating comprising a surfactant according to formula I. Fixed macrophages (histiocytes) abound in the liver, nervous system, lungs, lymph nodes, bone marrow, and several other tissues, and such cells also demonstrate enhanced uptake of the surface-modified particles according to the invention at least relative to particles not having a coating comprising a surfactant according to formula I. Tissues that are most affected by bacterial, viral or fungal pathogens and which are inflamed can be targeted by delivery of drug-loaded cells (granulocytes, for example) having a propensity to be directed to these inflammation sites by chemotaxis. Thus, by promoting uptake by the aforementioned cells, the pharmaceutical agent is released from these cells in a region where it is therapeutically most needed. Thus, delivery of the agent to a target tissue for treatment of a disease or disorder is facilitated by cells loaded with coated particles according to the invention. Such diseases and disorders include, but are not limited to, infectious diseases or disorders, inflammatory diseases or disorders, neurodegenerative diseases or disorders, and proliferative diseases or disorders.

There are numerous phagocytic cell types that are capable of enhanced uptake of coated particles. These cells include, but are not limited to, macrophages, monocytes, granulocytes, agranulocytes and neutrophils. The present invention also encompasses weakly phagocytic cells and non-phagocytic cells. Thus, other suitable cell types include, but are not limited to, T-lymphocytes, B-lymphocytes, null cells, natural killer cells, lymphocytes, red blood cells, muscle cells, bone marrow cells, stem cells, bone cells, vascular cells, organ tissue cells, neuronal cells, basophils, eosinophils, dendritic cells, and endothelial cells. Still other cells can be used to deliver the pharmaceutically active compounds to a subject. Any cell type may be used in the present invention so long as it is capable of uptake of the particle. Uptake by the cells of the particles may include phagocytosis, or other means of endocytosis, or attachment/adsorption of the particle onto the surface of the cells. Particles associated with the cell surface can also be taken into the cells by pinocytosis, which is an invagination of the cell membrane to form an intracellular capsule around the particle. In pinocytosis ("cell drinking"), the engulfed particle is relatively small (e.g., 20 nm) (Watts et al., Endocytosis: what goes in and how?, Journal of Cell Science, 1992, volume 103(1), pages 1-8). Pinocytosis occurs continuously in almost all eucaryotic cells. Diseased cells, for example, cancerous cells, can also demonstrate enhanced uptake of the surface modified particles according to the invention at least as compared to cells contacted with particles not having a coating comprising a surfactant of formula I.

As explained herein, the particles advantageously include a coating which facilitates cellular uptake. In particular, the coating can facilitate uptake by cells such as monocytes, macrophages, and T-lymphocytes, which are capable of trafficking by known mechanisms such as chemotaxis to a site of inflammation, infection, and/or tumor and thereby deliver the particles to a particular target tissue.

In one aspect of the invention, the contacting of the cells to the surface-modified particle (to form cells loaded with the active agent) is carried out ex vivo (i.e., outside of a mammalian subject). Alternatively, or in addition, the contacting of the cells to the surface-modified particle can be carried out in vivo (i.e., inside a mammalian subject). An amount of the surface modified particle that is effective to treat a disease or disorder is used during the contacting step. One of ordinary skill understands that a certain amount of the particles may be taken up by a cell type that does not traffic to a target tissue of interest, or is not released by the cell at the target tissue of interest. Therefore, one of ordinary skill understands that the amounts of particles administered may be optimized by routine protocols, provided that such amounts are within established administration protocols.

For ex-vivo administration, the cells can be isolated from a mammalian subject using a cell separator or apheresis device. For instance, the CS-3000™ cell separator (Fenwal Inc., Lake Zurich, Ill.) or the ISOLEX™ cell separator (Baxter Healthcare Corp., Deerfield, Ill.) can be used to isolate various cells. Other methods known to those skilled in the art of ex-vivo cell isolation can be employed to obtain cells useful in the present invention. Such methods include, but are not limited to, apheresis of peripheral blood, mobilization of bone marrow cells through, e.g., G-CSF, M-CSF, or GM-CSF, or direct removal of marrow cells by spinal, sternal, lumbar, or iliac crest puncture. The ex-vivo cells can be maintained in a cell culture medium or other isolating system known to those skilled in the art. Examples of such media are Alserver's Solution, Ames' Medium, Eagle's Basal Medium, CHO (Chinese Hamster Ovary) cell culture media, Click's Medium, Dulbecco's Modified Eagle's Medium, phosphate-buffered saline, phosphate-buffered dextrose or sucrose, Earle's Balanced Salt Solution, Gene Therapy Medium-3, Gey's Balanced Salt Solution, Glasgow Minimum Essential Medium, Hanks' Balanced Salt Solutions, Hybridoma Media, Iscove's Modified Dulbecco's Medium, Krebs-Henseleit Buffer with sugars, Leibovitz Media (L-15), M16 Medium, McCoy's Medium, MCDB, MDBK (Madin-Darby Bovine Kidney), MDCK (Madin-Darby Canine Kidney), Medium 199, NCTC, Ham's Media (e.g., Nutrient Mixture F-10), Coon's Modified Ham's Medium, RPMI, and others such as those listed in Biochemicals & Reagents for Life Science Research, Sigma-Aldrich Co. (St. Louis, Mo., USA). The purpose of the culture so described may be for the purpose of simple storage without loss of cells, or for cell proliferation or expansion, by appropriate addition of growth factors, cytokines, and nutrients, to encourage cell expansion. Such expansion would minimize the number of times that a patient would have to be prepared for removal of cellular samples.

Once isolated, the cells can be contacted with the coated particles and incubated for a short period of time to allow for cell uptake of the particles. The concentrations of particles used in the ex-vivo procedure will vary due to several factors, including, but not limited to, type of cells used, concentration of cells, active agent employed, size of the small particle dispersions, disease to be treated, and so on. Generally, however, the cellular isolates are contacted with about 1 to about 300 mg/ml of particles of the present invention. During contact of the particles with the cells, the particles are at a concentration higher than the thermodynamic saturation solubility, thereby allowing the particles to remain in particulate form during uptake and delivery to the mammalian subject. The cells can be incubated with the particles for up to 24 hours or longer to permit sufficient cell uptake of the drug particles.

Any method to effect uptake of particles of active agent by ex vivo cells can be used with the requirement that the method does not destroy or otherwise make the cells nonuseful for administration to a subject. For example, site-specific delivery of the particle via a biorecognition molecule may be used. See, e.g., U.S. Patent Publication No. 2003/0092069, incorporated herein by reference, which discloses the transferring of genes into specific cells or tissues via a hollow nanoparticle. Other methods of loading the ex-vivo cells include electroporation, sonoporation, and other mechanical means that disrupt the cell membrane (sonication, for example) and enable insertion of solid particulates into the cells. Ultrasound was successfully used by Zamitsyn et al. (Zamitsyn et al., Physical parameters influencing optimization of ultrasound-mediated DNA transfection, Ultrasound Med. Biol., 2004, volume 30(4), pages 527-538) to transiently disrupt cell membranes and thereby facilitate the loading of DNA into viable cells. Other mechanical procedures are well-known to those experienced in the art, and are included as part of this disclosure. Chemical methods of transiently destabilizing cell membranes are also well known. Transfection reagents contain surface active agents and include 293FECTIN™ Transfection Reagent and LIPOFECTAMINE™, both products of Invitrogen Corporation (Carlsbad, Calif.). Another example of a surfactant used to transfer DNA into cells is the SAINT™ reagent from Synvolux Therapeutics B. V. L. J. (Groningen, The Netherlands), which is based on a pyridinium surfactant.

The following description of particles also applies to all embodiments disclosed herein. For marginally soluble drugs, the cell loading procedure can be utilized provided that the cells are able to take up the coated active agent particles at a faster rate than the competing dissolution process. The particles should be of an appropriate size to allow for the cells to take up the coated particles and deliver them to the target tissue before complete dissolution of the particle. Because cells which are known to traffic to the target tissue of interest are capable of taking up the particles, the active agent is ultimately released from the cells or otherwise delivered in the vicinity of the target tissue. Furthermore, the concentration of the active agent composition should be kept higher than the saturation solubility of the composition so that the particle is able to remain in the crystalline state during uptake.

The following description of particles also applies to all embodiments disclosed herein. Administering of the surface-modified particle can be performed by various techniques known in the art for administering particles. Administering includes administering the surface-modified particle to a mammalian subject. Suitable methods for administering of the surface-modified particle include, but are not limited to, administering the particle intravenously, intraarterially, intramuscularly, subcutaneously, intradermally, intraarticularly, intrathecally, epidurally, intracerebrally, buccally, rectally, topically, transdermally, orally, intranasally, via the pulmonary route, intraperitoneally, and/or intraophthalmically. The step of administering can be by bolus injection, by intermittent infusion, or by continuous infusion. The amount of surface-modified particle and method of delivery can be determined by skilled clinicians. Various factors will affect the amount and method of delivery including, but not limited to, the type of cells used (for ex vivo methods of administration), the sex, weight and age of the subject to be treated, the type and maturity of the disease or disorder to be treated, the active agent to be administered, and so on. Generally, the active agent can be provided in doses ranging from 1 pg compound/kg body weight to 1000 mg/kg, 0.1 mg/kg to 100 mg/kg, 0.1 mg/kg to 50 mg/kg, and 1 to 20 mg/kg, given in daily doses or in equivalent doses at longer or shorter intervals, e.g., every other day, twice weekly, weekly, or twice or three times daily.

Various diseases or disorders can be treated by the present methods including, but not limited to, infectious diseases or disorders, inflammatory diseases or disorders, neurodegenerative diseases or disorders, and proliferative diseases or disorders. In this regard, symptoms of such diseases or disorders can be alleviated by the present methods.

"Infectious diseases or disorder" as used herein refers to a condition caused by pathogenic microorganisms, such as bacteria, viruses, parasites or fungi. Infectious diseases or disorders that can benefit from the disclosed methods include, but are not limited to, viral infections (including retroviral infections) such as dengue, enterovirus infections, HIV, hepatitis B, hepatitis C, and influenza; fungal infections; parasitic infections such as African trypanosomiasis and malaria; and bacterial infections such as cholera, meningitis, and tuberculosis.

"Inflammatory disease or disorder" as used herein refers to a condition characterized by redness, heat, swelling, and pain (i.e., inflammation) that typically involves tissue injury or destruction. Inflammatory diseases or disorders are notably associated with the influx of leukocytes and/or leukocyte chemotaxis. Inflammatory conditions may result from infection with pathogenic organisms or viruses and from noninfectious events including but not limited to trauma or reperfusion following myocardial infarction or stroke, immune responses to foreign antigens, and autoimmune responses. Accordingly, inflammatory conditions amenable to treatment with the methods and compounds of the invention encompass conditions associated with reactions of the specific defense system, conditions associated with reactions of the non-specific defense system, and conditions associated with inflammatory cell activation.

As used herein, the term "specific defense system" refers to the component of the immune system that reacts to the presence of specific antigens. Examples of inflammatory conditions resulting from a response of the specific defense system include but are not limited to the classical response to foreign antigens, autoimmune diseases, and delayed type hypersensitivity response mediated by B-cells and/or T-cells (i.e., B-lymphocytes and/or T-lymphocytes). Chronic inflammatory diseases, the rejection of solid transplanted tissue and organs including but not limited to kidney and bone marrow transplants, and graft versus host disease (GVHD), are further examples of inflammatory conditions resulting from a response of the specific defense system.

The term "non-specific defense system" as used herein refers to inflammatory conditions that are mediated by leukocytes that are incapable of immunological memory (e.g., granulocytes including but not limited to neutrophils, eosinophils, and basophils, mast cells, monocytes, macrophages). Examples of inflammatory conditions that result, at least in part, from a reaction of the non-specific defense system include but are not limited to adult (acute) respiratory distress syndrome (ARDS), multiple organ injury syndromes, reperfusion injury, acute glomerulonephritis, reactive arthritis, dermatitis with acute inflammatory components, acute purulent meningitis, other central nervous system inflammatory conditions including but not limited to stroke, thermal injury, inflammatory bowel disease, granulocyte transfusion associated syndromes, and cytokine-induced toxicity.

The therapeutic methods of the invention include methods for the amelioration of conditions associated with inflammatory cell activation. "Inflammatory cell activation" refers to the induction by a stimulus (including but not limited to cytokines, antigens, and auto-antibodies) of a proliferative cellular response, the production of soluble mediators (including but not limited to cytokines, oxygen radicals, enzymes, prostanoids, and vasoactive amines), or cell surface expression of new or increased numbers of mediators (including but not limited to major histocompatability antigens and cell adhesion molecules) in inflammatory cells (including but not limited to monocytes, macrophages, T lymphocytes, B lymphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

Other diseases or disorders which can be successfully treated include diseases or disorders characterized by inflammation or infection, including but not limited to, rheumatoid arthritis, Graves' disease, myasthenia gravis, thyroiditis, diabetes, inflammatory bowel disease, autoimmune oophoritis, systemic lupus erythematosus, and Sjögren's syndrome.

Examples of neurodegenerative diseases or disorders which can be successfully treated include, but are not limited to, Parkinson's disease, Alzheimer's disease, multiple sclerosis, encephalomyelitis, encephalitis (including HIV encephalitis), Huntington's disease, amyotrophic lateral sclerosis (also known as Lou Gehrig's disease), frontotemporal dementia, prion diseases, Creutzfeldt-Jakob disease, and adrenoleukodystrophy. Other neurodegenerative diseases or disorders which can be successfully treated include Pick's disease, frontotemporal lobar degeneration, progressive aphasia, and semantic dementia. Prion diseases, also known as transmissible spongiform encephalopathies (TSEs), include Creutzfeldt-Jakob disease, new variant Creutzfeldt-Jakob disease, Gerstmann-Sträussler-Scheinker syndrome, fatal familial insomnia, and kuru. The neurodegenerative diseases or disorders also can be Alexander disease, Alper's disease, ataxia telangiectasia, Batten disease (also known as Spielmeyer-Vogt-Sjogren-Batten disease), Canavan disease, Cockayne syndrome, corticobasal degeneration, HIV-associated dementia, Kennedy's disease, Krabbe disease, Lewy body dementia, Machado-Joseph disease (spinocerebellar ataxia type 3), multiple system atrophy, neuroborreliosis, Pelizaeus-Merzbacher disease, primary lateral sclerosis, Refsum's disease, Sandhoff disease, Schilder's disease, schizophrenia, spinocerebellar ataxia, spinal muscular atrophy, Steele-Richardson-Olszewski disease, and tabes dorsalis.

Proliferative diseases or disorders that can benefit from the disclosed methods include, but are not limited to, colon cancer, kidney cancer, non small cell lung cancer, small cell lung cancer, head and neck cancer, cancers of the peritoneal cavity (such as ovarian cancer), cervical cancer, breast cancer, prostate cancer, brain cancer (including glioma), sarcoma, melanoma, leukemia, acute lymphocytic leukemia, acute myelogenous leukemia, chronic lymphocytic leukemia, chronic myelogenous leukemia, Hodgkin lymphoma, non-Hodgkin lymphoma, myeloma, and glioblastoma. Thyroiditis includes Hashimoto's thyroiditis, subacute thyroiditis (also known as de Quervain's thyroiditis), silent thyroiditis (also known as painless thyroiditis), post partum thyroiditis, drug-induced thyroiditis, radiation-induced thyroiditis, and acute suppurative thyroiditis.

The disclosure may be better understood by reference to the following examples which are not intended to be limiting, but rather only set forth exemplary embodiments in accordance with the disclosure.

EXAMPLES

Example 1

Preparation of Paclitaxel Particles Having a DOTAP Coating

Paclitaxel particles were prepared using a microprecipitation/homogenization procedure. Specifically, paclitaxel (0.5 g) was dissolved in N-methylpyrrolidone (NMP) (3 g) and then added, with rotor-stator mixing, to aqueous surfactant solution A (25 mL). Solution A (pH ~7.8 to 8.0) contained sodium phosphate, dibasic, anhydrous (0.13 g), sodium phosphate, monobasic, monohydrate (0.01 g), glycerin (2.2 g), DSPE-mPEG 2000 (0.2 g), and poloxamer 188 (0.5 g) in 100 mL water (Table 1).

TABLE 1

| Component | % (w/v) for Solution A | % (w/v) for Solution B |
|---|---|---|
| Sodium phosphate, dibasic, anhydrous | 0.127 | 0.127 |
| Sodium phosphate, monobasic, monohydrate | 0.0144 | 0.0144 |
| Glycerin | 2.2 | 2.2 |
| DSPE-mPEG 2000 | 0.2 | 0.2 |
| Poloxamer 188 | 0.5 | 0.5 |
| DOTAP | 0.0 | 0.1 |
| Water | QS to 100 mL | QS to 100 mL |

The resulting suspension was transferred to a homogenizer (Avestin C5) and circulated at static pressure until the suspension temperature reached at least 50° C. The suspension was then homogenized at a target pressure of 20,000±2,000 psi and a target temperature of 60° C. for 60 minutes. The suspension was collected and centrifuged for 30 minutes at 10,000 rpm. Upon completion of the centrifuge cycle, the supernatant was decanted and replaced with an equal volume of aqueous surfactant solution B. Solution B (pH ~7.8 to 8.0) contained the same components as solution A and additionally contained N-[1-(2,3-dioleoyloxy)propyl]-N,N,N-trimethylammonium methylsulfate (DOTAP, 0.1 g) (Table 1). The pellet was resuspended, and the centrifugation was repeated twice more, using solution B as the replacement surfactant each time. After the third resuspension, the nanosuspension was homogenized for 30 minutes at a target pressure of 20,000±2,000 psi and a target temperature of 60° C. The final suspension contained particles having a size of ~160-170 nm.

Fluorescently-labeled paclitaxel particles were prepared according to the procedure above by adding fluorescently-labeled paclitaxel to the drug concentrate. Specifically, 400 μg Oregon Green-labeled paclitaxel (available from Invitrogen, Carlsbad, Calif.) was added to the drug concentrate described above to yield fluorescently-labeled paclitaxel particles with adequate fluorescence intensity to be detected in flow cytometry and fluorescent microscopy.

Example 2

Uptake by Human Mononuclear Cells of Paclitaxel Particles Having a DOTAP Coating The uptake of DOTAP-coated paclitaxel particles by human mononuclear cells was compared to the uptake of protamine-coated paclitaxel particles and DSPE-mPEG 2000/poloxamer 188-coated paclitaxel particles. The protamine-coated paclitaxel particles were prepared by adding 0.08 mL of a 25 mg/mL protamine solution to 0.01 mL of an Oregon Green-labeled paclitaxel suspension at 10 mg/mL.

Both DOTAP-coated particles and protamine-coated particles are slightly positively charged under the conditions used for the uptake experiments. Thus, the comparative experiment using protamine-coated paclitaxel particles was designed to assess whether enhanced uptake of paclitaxel particles could be solely attributed to the positive charge of the coated particles.

Figure 2A:
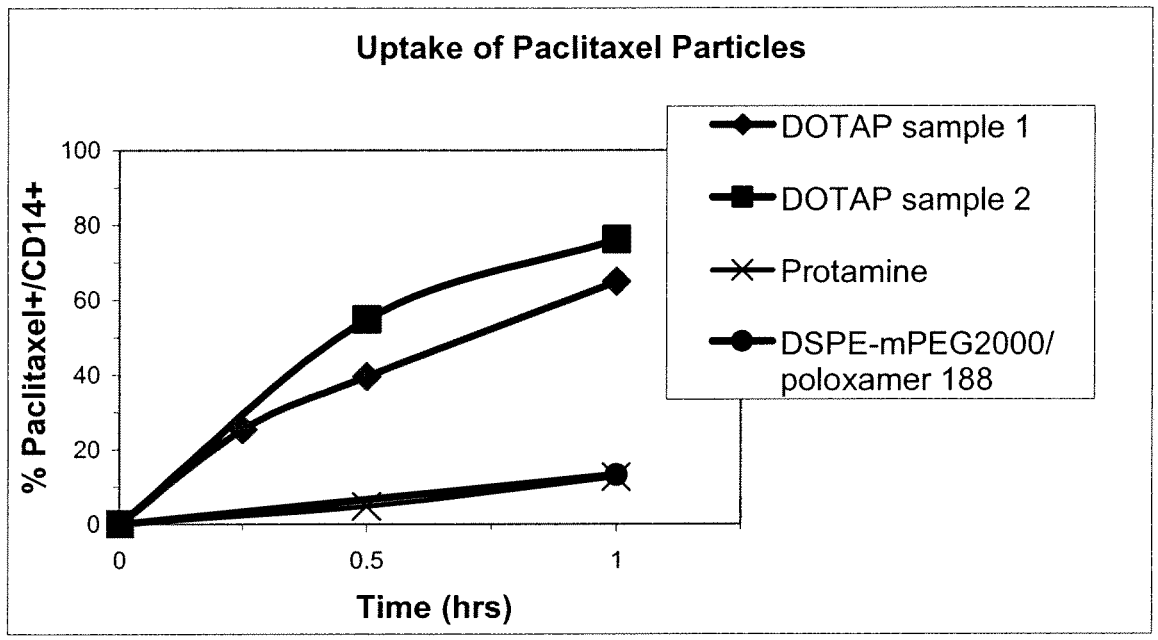
FIG. 2 provides graphs showing uptake of DSPE-mPEG2000/poloxamer 188-coated paclitaxel particles (DSPE-mPEG2000/poloxamer 188), DOTAP-coated paclitaxel particles labeled with Oregon Green and stored for 3 months (DOTAP Sample 1), freshly prepared DOTAP-coated paclitaxel particles labeled with Oregon Green (DOTAP Sample 2), and protamine-coated paclitaxel particles labeled with Oregon Green (Protamine).
Figure 2B:
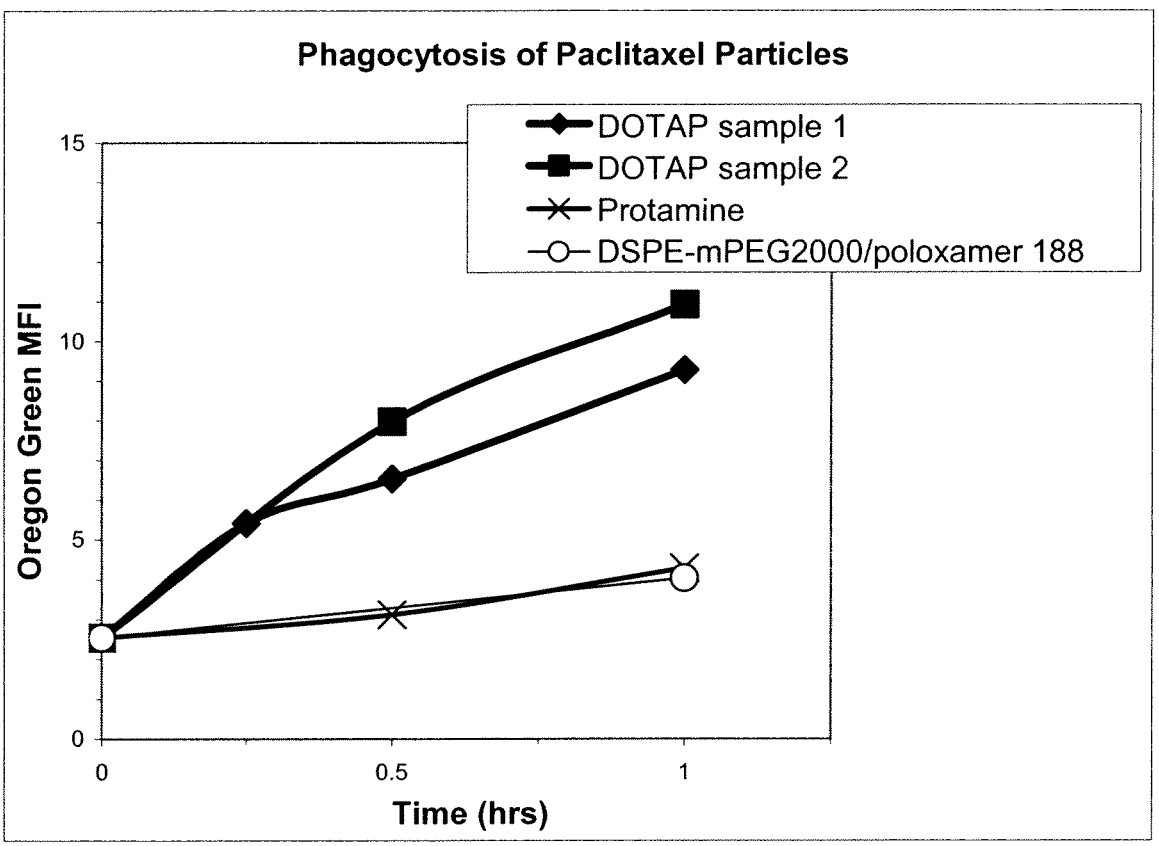
Figure 3A:
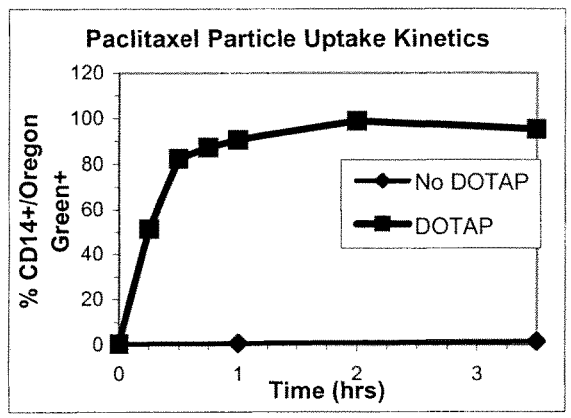
FIG. 3 provides graphs showing uptake of DSPE-mPEG2000/poloxamer 188-coated paclitaxel particles labeled with Oregon Green (No DOTAP) and DOTAP-coated paclitaxel particles labeled with Oregon Green (DOTAP). Cells were cultured for 1, 2, or 6 days prior to exposing the cells to the paclitaxel particles.
Figure 3B:
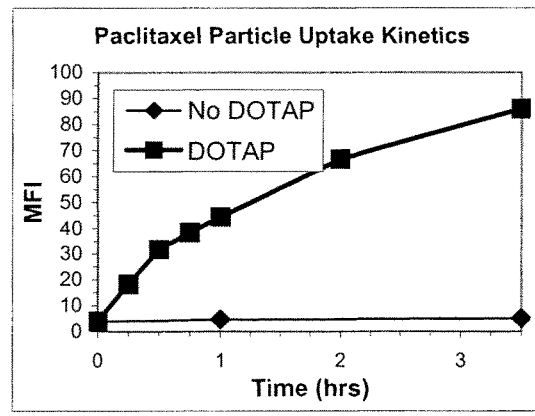
Figure 3C:
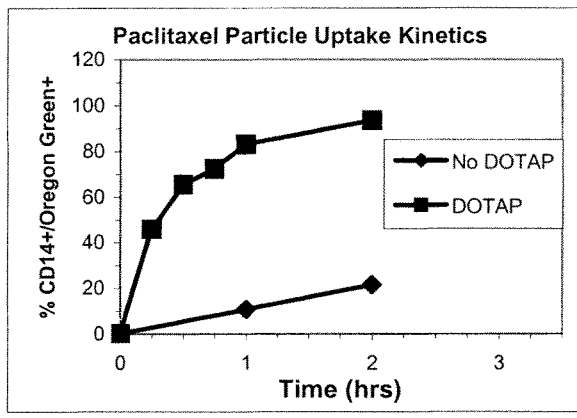
Figure 3D:
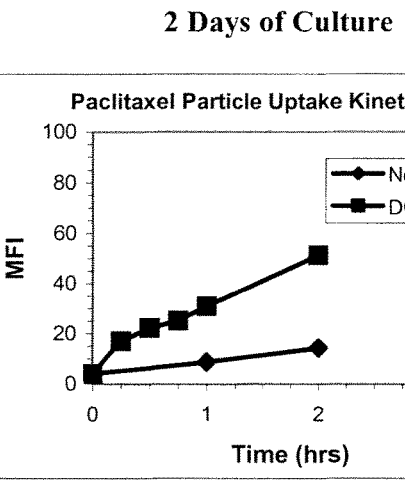
Figure 3E:
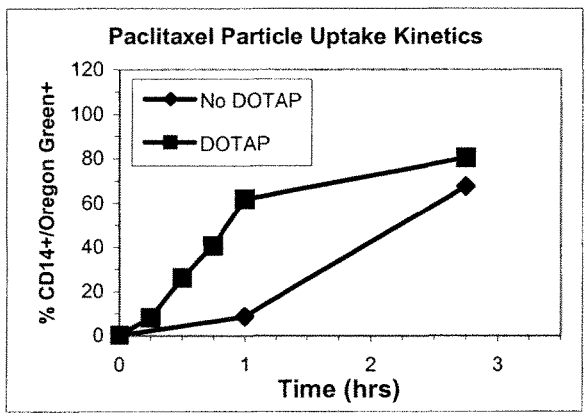
Figure 3F:
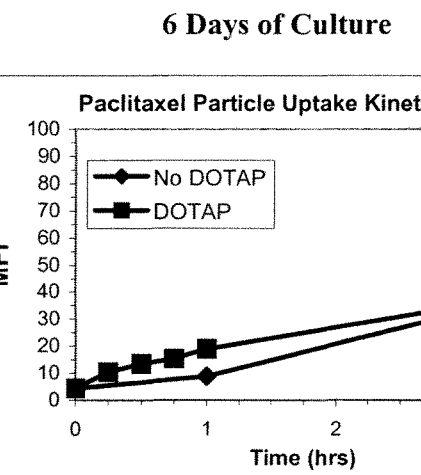

Zeta potential measurements were performed on the paclitaxel formulations used in the cell uptake experiments shown in FIG. 2 (and Table 2) by adding 30 µL suspension to 10 mL of 10 mM HEPES buffer pH 7.38. DOTAP- and protamine-coated paclitaxel nanoparticles have slightly positive zeta potentials, while DSPE-mPEG 2000/poloxamer 188-coated paclitaxel nanoparticles (which lack DOTAP or protamine) have a negative zeta potential under the tested conditions (data not shown).

Human mononuclear cells for use in the uptake experiments were purified from the whole blood of human donors. These cells were cultured in tissue culture treated 6-well plates (BD Biosciences) for 5-7 days in Media A, with media exchanged every 2-3 days. Media A contained DMEM (Gibco BRL cat. no. 11960-051) supplemented with the following to make 1 L: 1000 U/ml recombinant human macrophage-colony stimulating factor-1 (rhM-CSF-1) (Chemicon), 100 mL heat-inactivated human serum, 10 mL 200 mM L-glutamine (Gibco BRL cat. no. 25030-081), 2 mL 50 mg/ml Gentamicin (Sigma cat. no. G1397), and 400 µL 25 mg/mL Ciprofloxacin (Bayer code no. 89-001-1). The cells also were cultured on glass coverslips for microscopy applications.

The adherent monocyte-derived macrophages were then treated with paclitaxel formulations (paclitaxel particles having a DOTAP coating, paclitaxel particles having a protamine coating, or paclitaxel particles having a DSPE-mPEG 2000/poloxamer 188 coating) at 37° C. for various periods of time. The suspension formulations contained paclitaxel (doped with Oregon Green-labeled paclitaxel) at a final concentration of ~10 µM. After incubation, the cells were washed at least three times with 2 mL/well phosphate-buffered saline (PBS). The cells were then scraped in PBS and transferred to microfuge tubes (or fixed and mounted if the cells were adherent to coverslips).

To assess uptake of the paclitaxel particles, the cells were stained for CD14 expression and analyzed via flow cytometry. Gates were established based on the dot plots for both the isotype control (to establish the CD14+ selection gate) and the untreated cells (to establish the Oregon Green selection gate). Paclitaxel uptake was assessed by both the ratio of CD14+ cells (monocyte-derived macrophages) positive for Oregon Green fluorescence (% paclitaxel+/CD14+), i.e., the percentage of cells that have internalized or adsorbed paclitaxel particles, and the Mean Fluorescence Intensity (MFI). The MFI value directly correlates with the concentration of paclitaxel contained within the population of cells.

Figure 1B:
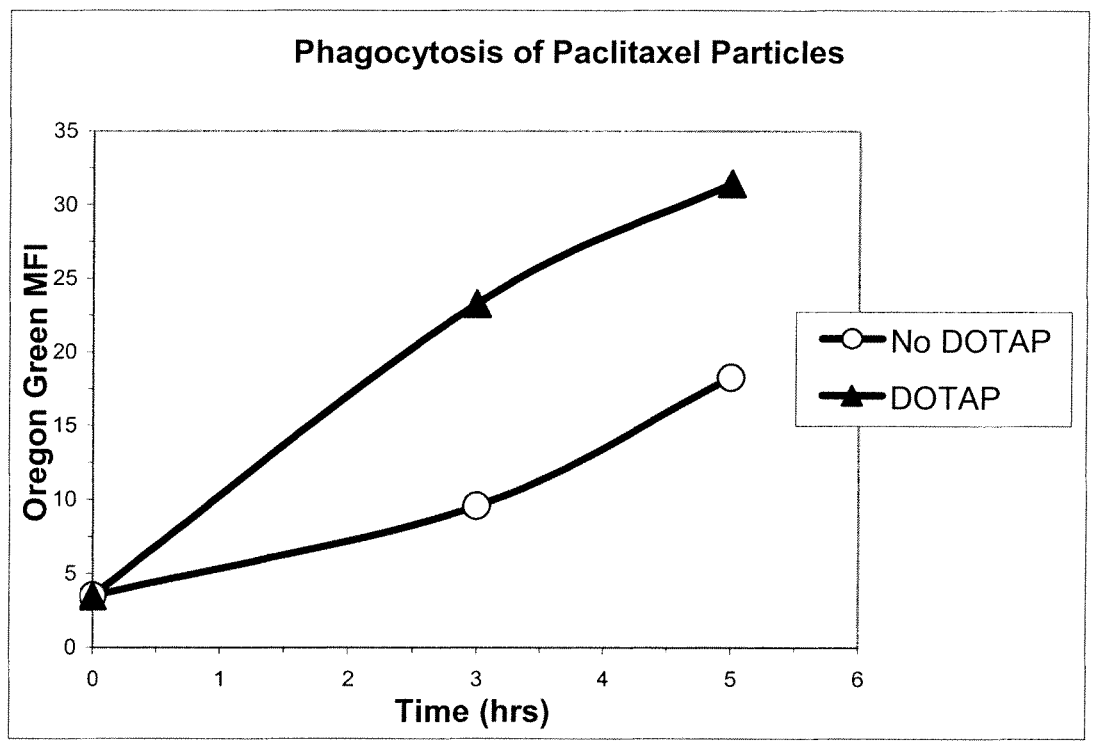

The uptake kinetics of the paclitaxel suspensions are shown in FIGS. 1 and 2 (results are shown as both percentages of paclitaxel positive cells after nanosuspension uptake and MFI of cell-associated/internalized particles). In FIG. 1, cells were exposed to the paclitaxel particles for 0, 3, 5 hours, while in FIG. 2, cells were exposed to the paclitaxel particles for 0, 0.25, 0.5, and 1 hour. The DOTAP coating substantially improved the uptake of paclitaxel particles as compared to DSPE-mPEG 2000/poloxamer 188-coated particles (FIGS. 1 and 2) and protamine-coated particles (FIG. 2). These results suggest that enhanced uptake of paclitaxel particles is not solely attributable to the positive charge of the coated particles.

Additionally, FIG. 2 demonstrates the stability of the paclitaxel formulations upon storage. DOTAP Sample 1 was stored for approximately 3 months prior to the uptake experiments. DOTAP Sample 2 was used in the uptake experiments shortly after preparation. These results indicate that storage of DOTAP-coated paclitaxel particles for several months does not significantly affect the particle uptake kinetics.

Uptake of paclitaxel particles was quantified by reverse phase HPLC. Paclitaxel uptake was measured after incubating the cells with the paclitaxel suspensions for 15, 30, and 60 minutes. Samples were prepared by adding acetonitrile (500 µL) to a 500 µL aliquot of each cell suspension and vortexing to mix. The samples were then centrifuged at 10,000 rpm for 30 minutes at 25° C. and the supernatants were analyzed by reverse phase HPLC to determine the amount of paclitaxel in the sample (Table 2).

TABLE 2

| Paclitaxel Levels in Cell Extracts (mg/mL) | | | |
|---|---|---|---|
| | 15 minutes | 30 minutes | 60 minutes |
| Untreated | — | — | 0.00030 |
| DOTAP sample 1 | 0.00083 | 0.00126 | 0.00177 |
| DOTAP sample 2 | — | 0.00148 | 0.00203 |
| Protamine | — | 0.00046 | 0.00082 |
| DSPE-mPEG 2000/ poloxamer 188 | — | — | 0.00082 |

FIG. 3 shows uptake by monocyte-derived macrophages of DOTAP-coated paclitaxel nanosuspensions after 1, 2, or 6 days of culture. The cells were exposed to the paclitaxel particles for various periods of time from 0 and 3.5 hours. The results indicate that the longer the cells are cultured, the less responsive they are to DOTAP-coated particles. It is theorized that the young cells (cells which have been cultured in vitro for relatively short periods of time) are capable of rapidly taking up DOTAP-coated particles, while relatively older cells (cells which have been cultured in vitro for longer periods of time) do not take up DOTAP-coated particles as readily.

Example 3

Uptake by Human Mononuclear Cells of Paclitaxel Particles Having a PLGA or a Phosphatidylserine Coating The uptake of DOTAP-coated paclitaxel particles was compared to the uptake of polylactic-co-glycolic acid (PLGA)-coated paclitaxel particles and to the uptake of phosphatidylserine (PS)-coated paclitaxel particles. PLGA-coated paclitaxel particles and PS-coated paclitaxel particles were prepared in accordance with the procedure described in Example 1, except that the PLGA particles were sonicated, rather than homogenized, and were formulated using a solution containing phosphate buffer, glycerin, PLGA, and Poloxamer 188, and the PS particles were formulated using a solution containing phosphate buffer, glycerin, DSPE-mPEG 2000, Poloxamer 188, and phosphatidylserine.

Figure 4A:
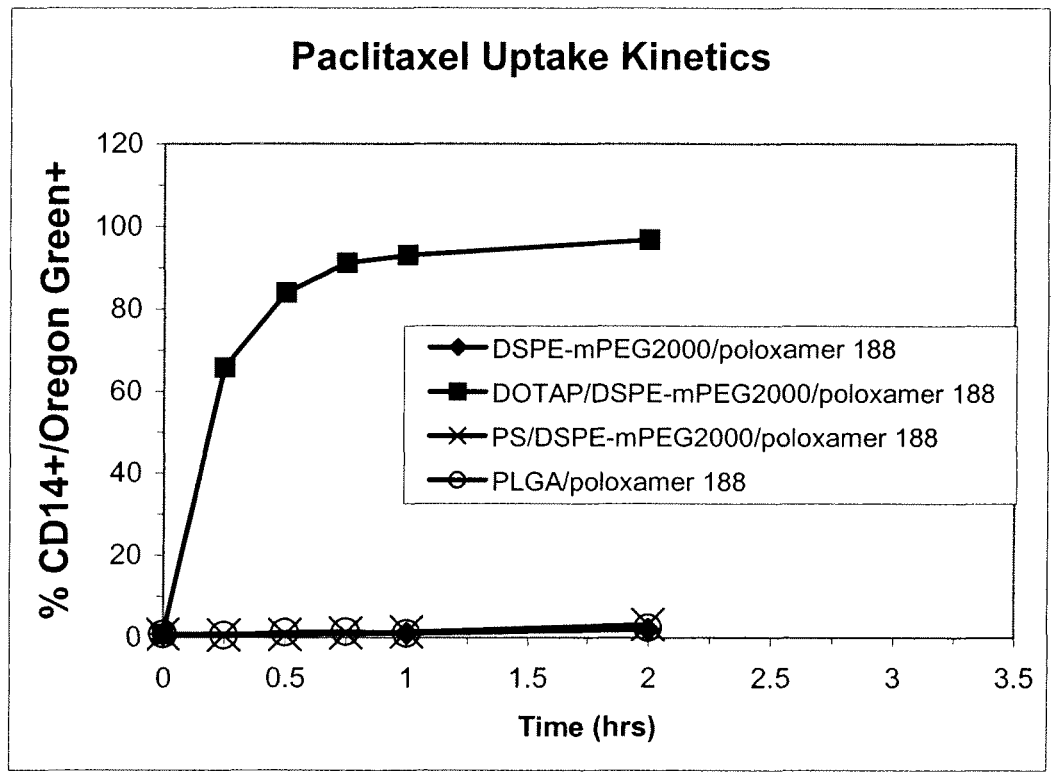
FIG. 4 provides graphs showing uptake of DSPE-mPEG2000/poloxamer 188-coated paclitaxel particles labeled with Oregon Green (DSPE-mPEG2000/poloxamer 188), DOTAP-coated paclitaxel particles labeled with Oregon Green (DOTAP/DSPE-mPEG2000/poloxamer 188), polylactic-co-glycolic acid-coated paclitaxel particles labeled with Oregon Green (PLGA/poloxamer 188), and phosphatidylserine-coated paclitaxel particles labeled with Oregon Green (PS/DSPE-mPEG2000/poloxamer 188).
Figure 4B:
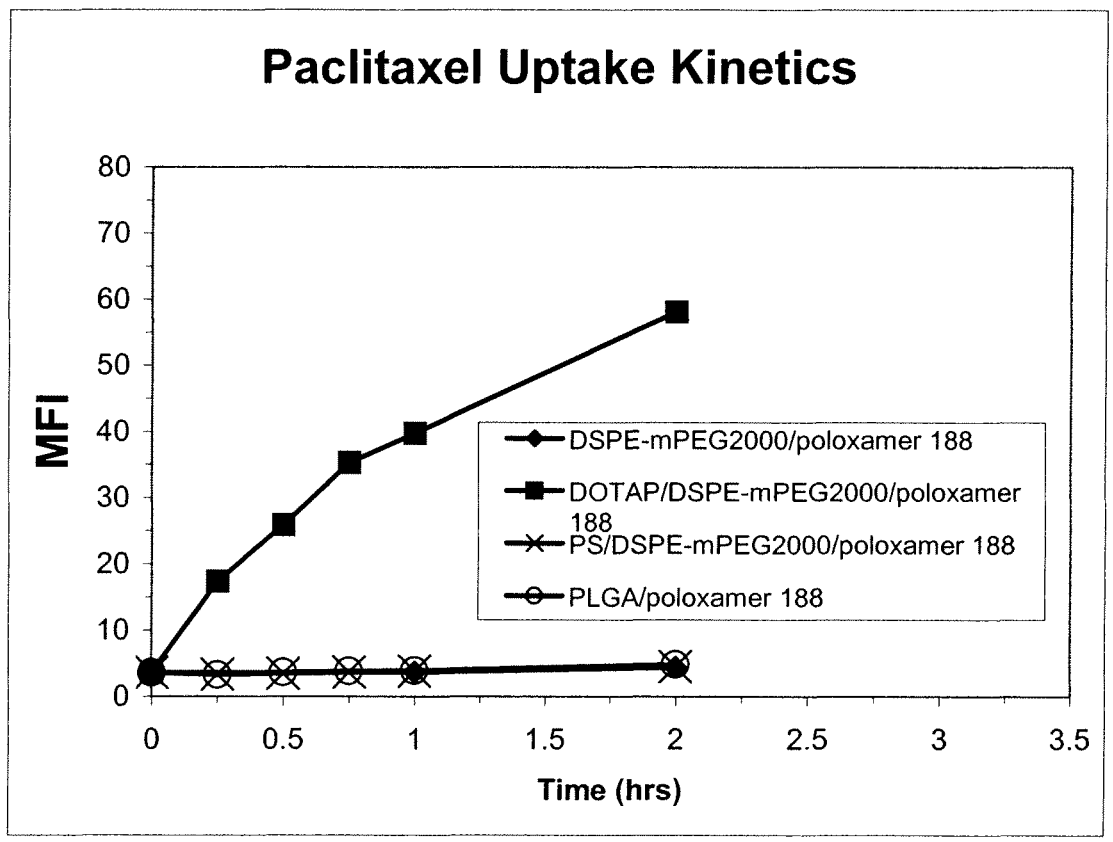
Figure 5A:
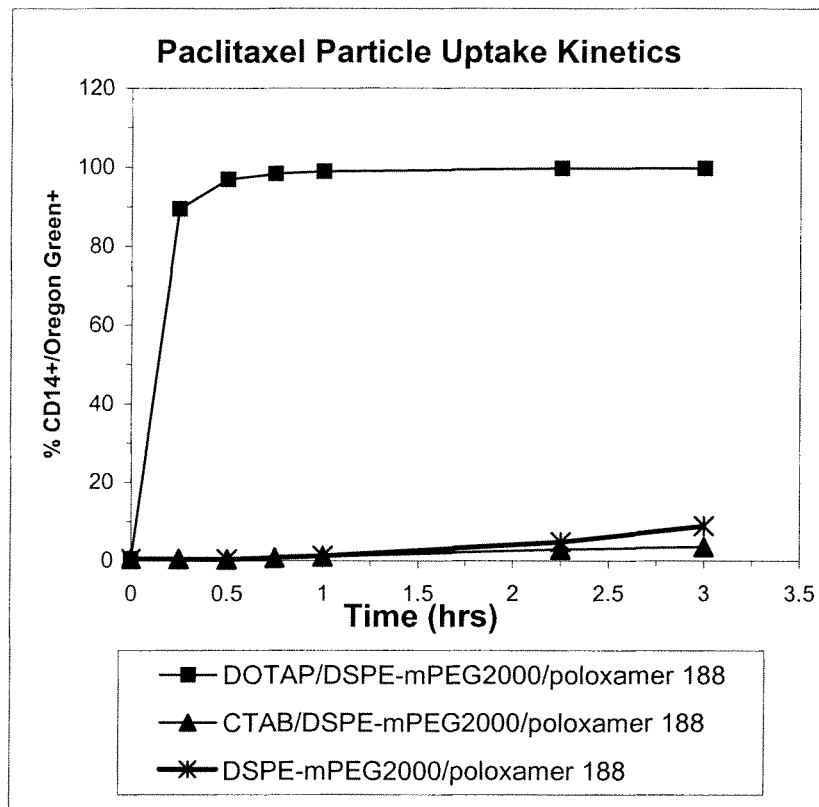
FIG. 5 provides graphs showing uptake of DSPE-mPEG2000/poloxamer 188-coated paclitaxel particles labeled with Oregon Green (DSPE-mPEG2000/poloxamer 188), DOTAP-coated paclitaxel particles labeled with Oregon Green (DOTAP/DSPE-mPEG2000/poloxamer 188), and cetyl trimethylammonium bromide-coated paclitaxel particles labeled with Oregon Green (CTAB/DSPE-mPEG2000/poloxamer 188).
Figure 5B:
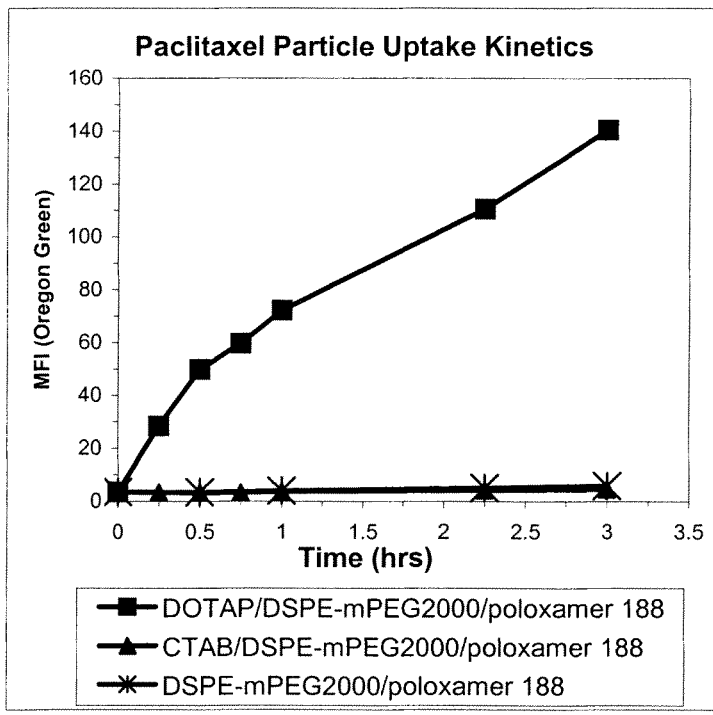
Figure 5C:
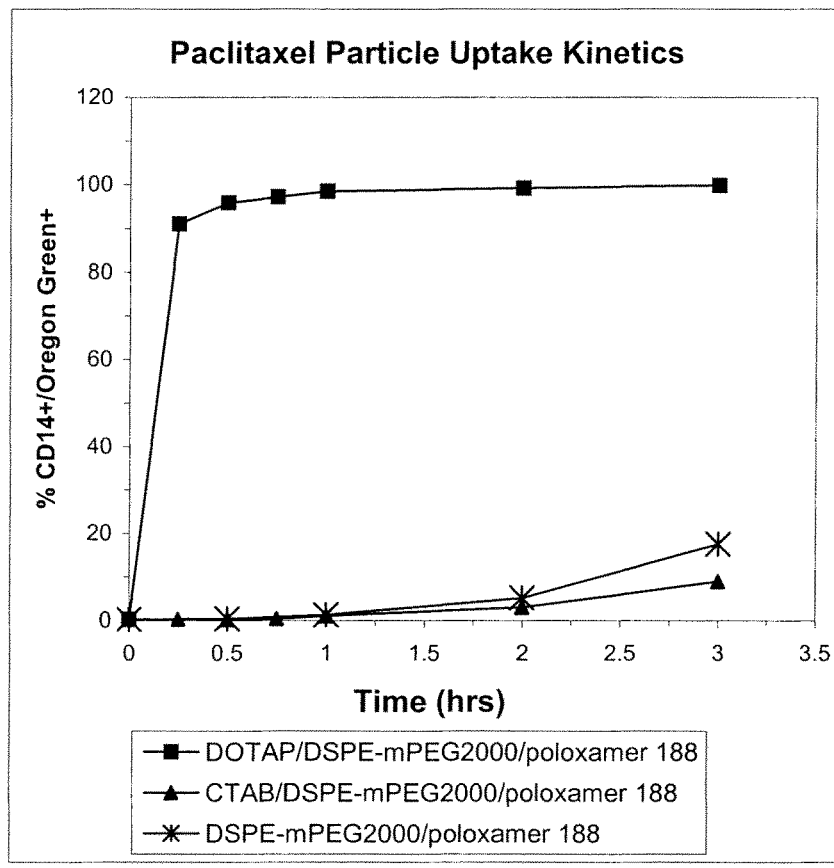
Figure 5D:
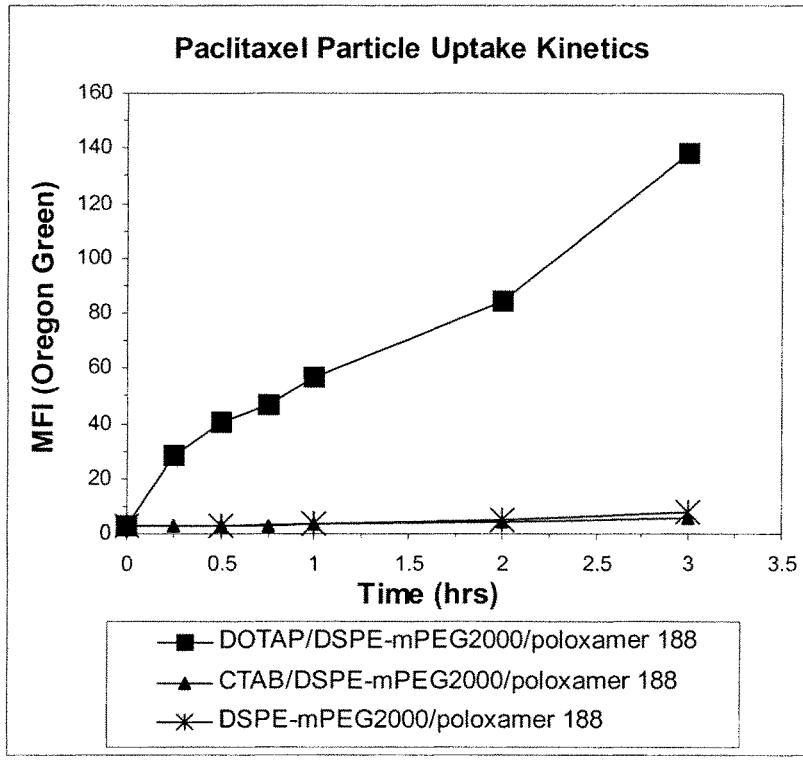

The uptake kinetics of the paclitaxel suspensions are shown in FIG. 4 (results are shown as both percentages of paclitaxel positive cells after nanosuspension uptake and MFI of cell associated/internalized particles). The DOTAP coating substantially improved the uptake of particles compared to PLGA-coated or phosphatidylserine-coated particles. These results suggest that enhanced uptake of paclitaxel particles is not solely attributable to the presence of a polymer or surfactant coating.

Example 4

Uptake by Human Mononuclear Cells of Paclitaxel Particles Having a CTAB Coating

The uptake of DOTAP-coated paclitaxel particles was compared to the uptake of cetyl trimethylammonium bromide (CTAB)-coated paclitaxel particles. CTAB-coated paclitaxel particles were prepared in accordance with the procedure described in Example 1, except that the CTAB particles were formulated using a solution containing phosphate buffer, glycerin, DSPE-mPEG 2000, Poloxamer 188, and CTAB.

The uptake kinetics of the paclitaxel suspensions are shown in FIG. 5 (results are shown as both percentages of paclitaxel positive cells after nanosuspension uptake and MFI of cell associated/internalized particles). The DOTAP coating substantially improved the uptake of particles compared to CTAB-coated particles. These results suggest that enhanced uptake of paclitaxel particles is not solely attributable to the presence of a coating having both a positively charged group and a hydrophobic group.

Example 5

Uptake of Paclitaxel Particles Having a DOTAP Coating in Whole Blood

Whole blood was drawn from a healthy human donor into EDTA vacutainer (BD Biosciences). Paclitaxel nanosuspensions doped with Oregon Green-labeled paclitaxel were incubated with the whole blood (~10 µM final concentration) for 1 hour at room temperature in 1.7 mL microfuge tubes on a tube rotator. A fraction of the whole blood was exposed to a hypotonic lysing solution (BD Biosciences) to lyse the red blood cells. The lysed samples were then stained for CD14 expression. Both the whole blood and stained cells were analyzed via flow cytometry.

No apparent increase in Oregon Green fluorescence was observed in either the red blood cell (RBC) or platelet populations. A substantial increase in fluorescence was observed in the CD14+ monocyte population in the lysed samples using the DOTAP-formulated paclitaxel suspension. Paclitaxel formulations having a DSPE-mPEG 2000/poloxamer 188 coating also showed some uptake in the CD14+ monocyte population. There was no apparent uptake in the other major cell populations as assessed by Oregon Green fluorescence (data not shown). These results suggest that DOTAP-coated paclitaxel particles are selectively taken up by monocytes over red blood cells, platelets, and other cell types present in blood.

Example 6

Uptake by Mouse Peritoneal Macrophages of Paclitaxel Particles Having a DOTAP Coating Peritoneal macrophages were isolated from mice and exposed to paclitaxel particles having a DOTAP coating and to paclitaxel particles without such a coating. Fluorescence images showed that peritoneal macrophages exposed to the DOTAP-coated particles took up greater amounts of paclitaxel than those exposed to DSPE-mPEG 2000/poloxamer 188-coated particles (data not shown). This example supports that DOTAP enhances uptake of particles by peritoneal macrophages.

Example 7

Uptake by Human OVCAR-3 Cells of Paclitaxel Particles Having a DOTAP Coating

Human OVCAR-3 cells were transfected with Red Fluorescent Protein (RFP) such that they fluoresced red. These cells were then exposed to paclitaxel particles prepared using Oregon Green-paclitaxel having a DOTAP coating and to paclitaxel particles without a DOTAP coating. Fluorescence images showed that the RFP-OVCAR-3 cells only took up particles when the particles were coated with DOTAP (data not shown). There was no visible uptake of the particles coated with DSPE-mPEG 2000/poloxamer 188. This example supports that DOTAP enhances uptake of particles by human ovarian cancer cells.

Example 8

Residence Time in Mice of Paclitaxel Particles Having a DOTAP Coating

Oregon Green-labeled paclitaxel particles having a DOTAP coating were injected subcutaneously into a mouse. Fluorescence images were captured over time to demonstrate particle residence time. The persistence of green fluorescence at 30 days indicated that paclitaxel particles remained for at least 30 days when injected subcutaneously (data not shown).

In a separate experiment, Oregon Green-labeled paclitaxel particles having a coating containing DOTAP and a rhodamine-labeled surfactant (Lissamine rhodamine B 1,2-dihexadecanoyl-sn-glycero-3-phosphoethanolamine, tri ethylammonium salt (rDHPE); Invitrogen, Carlsbad, Calif.) were injected intraperitoneally (IP) into a healthy mouse. Fluorescence images were captured over time to demonstrate particle residence time. The data indicated that paclitaxel nanoparticles were cleared rapidly (within about 24 hours) from the peritoneal space in a healthy mouse (data not shown).

A mouse model was established wherein test mice were implanted with RFP-OVCAR-3 cells and tumors were allowed to grow. The tumors expressed PFP and had red fluorescence. Oregon Green-labeled paclitaxel particles having a DOTAP coating were administered by intraperitoneal injection to mice having RFP-expressing tumors. The presence and location of the DOTAP-coated paclitaxel particles were detected relative to the tumors using fluorescence.

Both tumors and paclitaxel particles were observed by fluorescence microscopy (red fluorescence for tumors, green fluorescence for particles). Unlike healthy mice, in which particles were rapidly cleared from the peritoneal cavity, the DOTAP-coated paclitaxel particles were present in the tumor-bearing mice up to 30 days post-injection, indicating that the tumors present in the peritoneal cavity of the mouse were partially responsible for the increased residence time. Moreover, the DOTAP-coated paclitaxel particles frequently co-localized with tumors. Thus, this example supports that the DOTAP-coated paclitaxel particles target tumor sites as opposed to healthy tissues, and are able to persist within the targeted tumor sites for significant periods of time such that they can effectively deliver a sustained release of the therapeutic drug.

Additionally, when DOTAP-coated paclitaxel particles were present, the red fluorescence intensity diminished over time, consistent with tumor cell death. Conversely, in the absence of paclitaxel particles, the red fluorescence intensified over time. Thus, this example further demonstrates that administration of DOTAP-coated paclitaxel particles effectively treated cancer in vivo.

While specific embodiments have been illustrated and described, numerous modifications come to mind without departing from the spirit of the invention and the scope of protection is only limited by the scope of the accompanying claims.

What is claimed is:

1. A surface-modified particle comprising a particle core and a coating adsorbed to a surface of the particle core, wherein the particle core consists of a small molecule active agent, the coating comprises a surfactant having formula I, and the surface-modified particle has a size from about 10 nm to about 1 µm, does not comprise polysaccharides, does not comprise colloidal silicon dioxide, and does not comprise monoacylated monoglycerides:

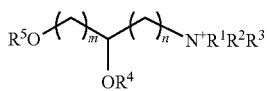

wherein n and m are 1;
$R^1$, $R^2$, and $R^3$ are methyl; and
$R^4$ and $R^5$ are independently selected from the group consisting of cis-9-octadecenoyl and cis-9-octadecenyl.

2. The particle of claim 1, wherein $R^4$ and $R^5$ are cis-9-octadecenoyl.

3. The particle of claim 1, wherein $R^4$ and $R^5$ are cis-9-octadecenyl.

4. The particle of claim 1, wherein the coating further comprises a second surfactant.

5. The particle of claim 4, wherein the second surfactant is selected from the group consisting of anionic surfactants, cationic surfactants, zwitterionic surfactants, nonionic surfactants, surface active biological modifiers, and combinations thereof.

6. The particle of claim 4, wherein the second surfactant comprises at least one of a poloxamer and a phospholipid.

7. The particle of claim 1, wherein the active agent is a therapeutic agent.

8. The particle of claim 7, wherein the therapeutic agent is selected from the group consisting of analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antifungals, antifibrotic agents, anti-infective agents, anti-parasitic agents, antihistamines, antimuscarinic agents, antimycobacterial agents, antineoplastic agents, antiprotozoal agents, antiviral agents, anxiolytic sedatives, beta-adrenoceptor blocking agents, corticosteroids, cough suppressants, dopaminergics, hemostatics, hematological agents, hypnotics, immunological agents, muscarinics, parasympathomimetics, prostaglandins, radio-pharmaceuticals, sedatives, stimulants, sympathomimetics, vitamins, xanthines, growth factors, hormones, antiprion agents, and combinations thereof.

9. The particle of claim 1, wherein the active agent is an antineoplastic agent selected from the group consisting of paclitaxel, paclitaxel derivative compounds, alkaloids, antimetabolites, enzyme inhibitors, alkylating agents, and combinations thereof.

10. The particle of claim 1, wherein the active agent is paclitaxel;
and R4 and R5 are cis-9-octadecenoyl.

11. The particle of claim 1, wherein the active agent is paclitaxel; and $R^4$ and $R^5$ are cis-9-octadecenyl.

12. The particle of claim 1, wherein the active agent is a protease inhibitor.

13. The particle of claim 12, wherein the protease inhibitor is selected from the group consisting of indinavir, ritonavir, saquinavir, nelfinavir, and combinations thereof.

14. The particle of claim 1, wherein the active agent is a nucleoside reverse transcriptase inhibitor.

15. The particle of claim 14, wherein the nucleoside reverse transcriptase inhibitor is selected from the group consisting of zidovudine, didanosine, stavudine, zalcitabine, lamivudine and combinations thereof.

16. The particle of claim 1, wherein the active agent is a non-nucleoside reverse transcriptase inhibitor.

17. The particle of claim 16, wherein the non-nucleoside reverse transcriptase inhibitor is selected from the group consisting of efavirenz, nevirapine, delaviradine, and combinations thereof.

18. The particle of claim 1, wherein the active agent is an anti-inflammatory agent.

19. The particle of claim 18, wherein the anti-inflammatory agent is selected from the group consisting of non-steroidal anti-inflammatory drugs, nonselective cycloxygenase (COX) inhibitors, COX-1 inhibitors, COX-2 inhibitors, lipoxygenase inhibitors, corticosteroids, anti-oxidants, tumor necrosis factor (TNF) inhibitors, and combinations thereof.

20. The particle of claim 1, wherein the active agent is selected from the group consisting of celecoxib, rofecoxib, valdecoxib, parecoxib, lumiracoxib, etoricoxib, and combinations thereof.

21. A pharmaceutical composition comprising a plurality of particles of claim 1.

22. A method of enhancing cellular uptake of an active agent, said method comprising:
contacting cells with surface-modified particles under conditions sufficient to enhance cellular uptake of the surface-modified particles, said particles comprising a particle core and a coating adsorbed to a surface of the particle core, wherein the particle core consists of a small molecule active agent, the coating comprises a surfactant having formula I, and the surface-modified particle has a size from about 10 nm to about 1 µm, does not comprise polysaccharides, does not comprise colloidal silicon dioxide, and does not comprise monoacylated monoglycerides:

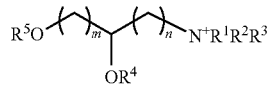

wherein n and m are 1;
$R^1$, $R^2$, and $R^3$ are methyl; and
$R^4$ and $R^5$ are independently selected from the group consisting of cis-9-octadecenoyl and cis-9-octadecenyl.

23. The method of claim 22, wherein the cells are phagocytic cells.

24. The method of claim 22, wherein said contacting is carried out ex vivo.

25. The method of claim 22, wherein said contacting is carried out in vivo.

26. The method of claim 22, wherein the cells are phagocytic cells selected from the group consisting of macrophages, monocytes, granulocytes, agranulocytes, neutrophils, and combinations thereof.

27. The method of claim 22, wherein said contacting is effected by administering to a subject an amount of said surface modified particles effective to treat infectious diseases or disorders, inflammatory diseases or disorders, neurodegenerative diseases or disorders, or proliferative diseases or disorders.

28. The method of claim 27, wherein said administering is performed intravenously, intraarterially, intramuscularly, subcutaneously, intradermally, intraarticularly, intrathecally, epidurally, intracerebrally, buccally, rectally, topically, transdermally, orally, intranasally, via the pulmonary route, intraperitoneally, intraophthalmically, or by a combination thereof.

29. The method of claim 27, wherein the subject has a neurodegenerative disease or disorder selected from the group consisting of Parkinson's disease, Alzheimer's disease, multiple sclerosis, encephalomyelitis, encephalitis, Huntington's disease, amyotrophic lateral sclerosis, frontotemporal dementia, prion diseases, Creutzfeldt-Jakob disease, and adrenoleukodystrophy.

30. The method of claim 27, wherein the subject has an inflammatory disease or disorder selected from the group consisting of rheumatoid arthritis, Graves' disease, myasthenia gravis, thyroiditis, diabetes, inflammatory bowel disease, autoimmune oophoritis, systemic lupus erythematosus, and Sjogren's syndrome.

31. The method of claim 27, wherein the subject has a proliferative disease or disorder selected from the group consisting of colon cancer, kidney cancer, non small cell lung cancer, small cell lung cancer, head and neck cancer, cancers of the peritoneal cavity, cervical cancer, breast cancer, prostate cancer, brain cancer, sarcoma, melanoma, leukemia, acute lymphocytic leukemia, acute myelogenous leukemia, chronic lymphocytic leukemia, chronic myelogenous leukemia, Hodgkin lymphoma, non-Hodgkin lymphoma, myeloma, and glioblastoma.

32. The method of claim 27, wherein the subject has a proliferative disease or disorder; and $R^4$ and $R^5$ are cis-9-octadecenoyl.

33. The method of claim 27, wherein the subject has a proliferative disease or disorder; and $R^4$ and $R^5$ are cis-9-octadecenyl.

34. A method for treating a subject having an infectious disease or disorder, an inflammatory disease or disorder, a neurodegenerative disease or disorder, or a proliferative disease or disorder comprising administering to said subject a plurality of surface-modified particles into a body cavity having a site of disease or inflammation, said surface-modified particles comprising a particle core and a coating adsorbed to a surface of the particle core, wherein the particle core consists of a small molecule active agent, the coating comprises a surfactant of formula I, the surface-modified particle has a size from about 10 nm to about 1 μm, does not comprise polysaccharides, does not comprise colloidal silicon dioxide, and does not comprise monoacylated monoglycerides, and said administration is effective in alleviating, treating, and/or preventing symptoms or pathologies associated with said disease or disorder:

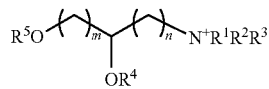

I wherein n and m are 1;
$R^1$, $R^2$, and $R^3$ are methyl; and
$R^4$ and $R^5$ are independently selected from the group consisting of cis-9-octadecenoyl and cis-9-octadecenyl.

35. The method of claim 34, wherein the body cavity is selected from the group consisting of the peritoneal cavity, the bladder cavity, the pulmonary cavity, the pleural cavity, the cardiac cavity, the aqueous humor of the eye, and the vitreous humor of the eye.

36. The method of claim 34, wherein the disease or disorder is cancer and the active agent is an antineoplastic agent.

37. The particle of claim 1, wherein the particles are amorphous, semicrystalline, crystalline, or a combination thereof.

38. The particle of claim 1, wherein the surface-modified particle is capable of dissolution when taken up by cells or delivered to tissue of a mammalian subject.

39. The particle of claim 1, wherein the surface-modified particle includes at least 75% (w/w) active agent.

40. The method of claim 22, wherein the surface-modified particle includes at least 75% (w/w) active agent.

41. The method of claim 34, wherein the surface-modified particle includes at least 75% (w/w) active agent.

* * * * *